US012773285B2

(12) United States Patent
Ke et al.

(10) Patent No.: US 12,773,285 B2
(45) Date of Patent: Oct. 27, 2026

(54) METHODS AND SYSTEMS FOR CONTROLLING IMAGE-GUIDED INTERVENTIONAL PUNCTURE DEVICES

(71) Applicant: WUHAN UNITED IMAGING SURGICAL CO., LTD., Wuhan (CN)

(72) Inventors: Xianfeng Ke, Wuhan (CN); Qiang Xie, Shanghai (CN)

(73) Assignee: WUHAN UNITED IMAGING SURGICAL CO., LTD., Wuhan (CN)

( * ) Notice: Subject to any disclaimer, the term of this patent is extended or adjusted under 35 U.S.C. 154(b) by 74 days.

(21) Appl. No.: 18/759,742

(22) Filed: Jun. 28, 2024

(65) Prior Publication Data

US 2024/0350211 A1 Oct. 24, 2024

Related U.S. Application Data

(63) Continuation of application No. PCT/CN2022/135624, filed on Nov. 30, 2022.

(30) Foreign Application Priority Data

Dec. 30, 2021 (CN) ......................... 202111660066.X

(51) Int. Cl.
*A61B 34/30* (2016.01)
*A61B 17/34* (2006.01)
(Continued)

(52) U.S. Cl.
CPC .......... *A61B 34/30* (2016.02); *A61B 17/3403* (2013.01); *A61B 34/10* (2016.02);
(Continued)

(58) Field of Classification Search
CPC ...... B25J 9/1697; B25J 9/1682; B25J 9/1669; B25J 9/1666; B25J 9/1676; B25J 9/1664;
(Continued)

(56) References Cited

U.S. PATENT DOCUMENTS 6,094,590 A * 7/2000 Kan ...................... A61B 90/36
600/411
2011/0276179 A1* 11/2011 Banks .................... A61B 34/30
700/264
(Continued)

FOREIGN PATENT DOCUMENTS

CN 107970060 A 5/2018
CN 110051436 A 7/2019
(Continued)

OTHER PUBLICATIONS

Li, Shenglin et al., Overview of the Vascular Interventional Surgery Robot, Chinese Journal of Medical Instrumentation, 37(2): 119-122, 2013.
(Continued)

*Primary Examiner* — Khoi H Tran
*Assistant Examiner* — Tanner L Cullen
(74) *Attorney, Agent, or Firm* — Poseidon Advanced IP LLC

(57) ABSTRACT

Embodiments of the present disclosure provide a method and system for controlling an image-guided interventional puncture device. The method may include: obtaining an initial movement state of an imaging device and/or a surgical robot; controlling a target movement state of the surgical robot and/or the imaging device based on the initial movement state.

16 Claims, 7 Drawing Sheets

(51) Int. Cl.

| | |
|---|---|
| ***A61B 34/00*** | (2016.01) |
| ***A61B 34/10*** | (2016.01) |
| ***A61B 34/37*** | (2016.01) |
| ***A61B 90/00*** | (2016.01) |

(52) U.S. Cl.
CPC .............. *A61B 34/25* (2016.02); *A61B 34/37* (2016.02); *A61B 90/361* (2016.02); *A61B 2034/107* (2016.02); *A61B 2034/258* (2016.02)

(58) Field of Classification Search
CPC ......... A61B 34/01; A61B 34/03; A61B 34/07; G05B 2219/39109; G05B 19/41815; G05B 2219/39114; G05B 2219/40287; G05B 2219/31008; G05B 2219/31089; G05B 2219/39101; G05B 2219/39118; G05B 2219/39175
See application file for complete search history.

(56) References Cited

U.S. PATENT DOCUMENTS

| | | | | |
|---|---|---|---|---|
| 2012/0190966 | A1* | 7/2012 | Schaerer | A61B 5/0064 600/411 |
| 2014/0163736 | A1* | 6/2014 | Azizian | A61B 34/20 700/259 |
| 2014/0324070 | A1 | 10/2014 | Min et al. | |
| 2016/0157887 | A1* | 6/2016 | Kim | A61B 5/746 600/424 |
| 2016/0249991 | A1 | 9/2016 | Glozman et al. | |
| 2016/0302871 | A1 | 10/2016 | Gregerson et al. | |
| 2017/0189126 | A1* | 7/2017 | Weir | A61B 34/25 |
| 2017/0210008 | A1* | 7/2017 | Maeda | B25J 9/1682 |
| 2018/0296290 | A1* | 10/2018 | Namiki | A61B 1/00009 |
| 2019/0090954 | A1 | 3/2019 | Kotian et al. | |
| 2021/0107151 | A1* | 4/2021 | Wouhaybi | B25J 9/1661 |
| 2021/0275263 | A1 | 9/2021 | Parrini et al. | |
| 2021/0401521 | A1* | 12/2021 | Mantri | A61B 34/30 |
| 2022/0241975 | A1* | 8/2022 | Tan | B25J 9/1661 |
| 2023/0001568 | A1* | 1/2023 | Vannuffelen | B25J 9/0081 |
| 2023/0133825 | A1* | 5/2023 | Row | A61B 34/20 700/245 |
| 2023/0339109 | A1* | 10/2023 | Balicki | B25J 13/085 |

FOREIGN PATENT DOCUMENTS

| | | | | |
|---|---|---|---|---|
| CN | 110584784 A | | 12/2019 | |
| CN | 110623731 A | | 12/2019 | |
| CN | 110664484 A | | 1/2020 | |
| CN | 111202583 A | | 5/2020 | |
| CN | 111513849 A | | 8/2020 | |
| CN | 211534702 U | | 9/2020 | |
| CN | 212879562 U | | 4/2021 | |
| CN | 114305613 A | | 4/2022 | |
| EP | 2561821 A1 | | 2/2013 | |
| JP | H10315170 A | * | 12/1998 | G05B 19/4141 |
| WO | 2016168671 A1 | | 10/2016 | |
| WO | 2016175489 A1 | | 11/2016 | |
| WO | 2017043926 A1 | | 3/2017 | |
| WO | WO-2022160509 A1 | * | 8/2022 | G06T 17/00 |

OTHER PUBLICATIONS

International Search Report in PCT/CN2022/135624 mailed on Feb. 16, 2023, 6 pages.
Written Opinion in PCT/CN2022/135624 mailed on Feb. 16, 2023, 7 pages.

* cited by examiner

METHODS AND SYSTEMS FOR CONTROLLING IMAGE-GUIDED INTERVENTIONAL PUNCTURE DEVICES

CROSS-REFERENCE TO RELATED APPLICATION

The present disclosure is a Continuation of International Application No. PCT/CN2022/135624, filed on Nov. 30, 2022, which claims priority to Chinese application No. 202111660066. X, filed on Dec. 30, 2021, the entire contents of each of which are incorporated herein by reference.

TECHNICAL FIELD

The present disclosure relates to the field of medical devices, and in particular, to methods and systems for controlling an image-guided interventional puncture device.

BACKGROUND

With the development of electronic computed tomography (CT) technology and surgical robots, guiding surgical robots for CT imaging devices are increasingly being used to assist physicians in performing puncture operations. Automatic needle insertion by surgical robots or physician-led surgical robotics has become a major development trend in interventional puncture operations with CT imaging devices.

In order to realize a CT imaging device guiding a surgical robot to complete a puncture action, it is generally necessary to obtain location information of a specific region within the patient's body through the CT imaging device, and then guide the surgical robot to that location to complete the puncture action. However, since the image-guided interventional puncture system is often independent of the CT system, the CT imaging device is unable to detect the operating state of the surgical robot while it is operating, and the surgical robot is unable to detect the operating state of the CT imaging device while it is operating, which tends to result in unintended relative movement of the surgical robot and the CT imaging device, causing injury to the patient.

Accordingly, it is desired to provide a method and system for controlling an image-guided interventional puncture device, so as to address the problem of possible unintended relative movement of a surgical robot and a CT imaging device.

SUMMARY

One of the embodiments of the present disclosure provides a method of controlling an image-guided interventional puncture device. The method may comprise obtaining an initial movement state of an imaging device and/or a surgical robot; and controlling a target movement state of the surgical robot and/or the imaging device based on the initial movement state.

In some embodiments, the controlling a target movement state of the surgical robot and/or the imaging device based on the initial movement state may include: controlling a second movement state of the surgical robot based on a first movement state of the imaging device; and/or controlling the first movement state of the imaging device based on the second movement state of the surgical robot.

In some embodiments, the controlling a second movement state of the surgical robot based on a first movement state of the imaging device may include: in response to a determination that the imaging device is in movement, controlling the surgical robot to remain stationary based on the first movement state of the imaging device.

In some embodiments, the controlling the first movement state of the imaging device based on the second movement state of the surgical robot may include: in response to a determination that the surgical robot is in movement, controlling the imaging device to remain stationary based on the second movement state of the surgical robot.

In some embodiments, the controlling a second movement state of the surgical robot based on a first movement state of the imaging device may include: determining a first movement trajectory of the imaging device based on the first movement state of the imaging device; and controlling, based on the first movement trajectory, the surgical robot to move.

In some embodiments, the controlling, based on the first movement trajectory, the surgical robot to move may include: predicting a distance between the imaging device and the surgical robot based on the first movement trajectory of the imaging device; and in response to the distance being less than a distance threshold, controlling both the imaging device and the surgical robot to remain stationary.

In some embodiments, the controlling, based on the first movement trajectory, the surgical robot to move may include: planning a second movement trajectory of the surgical robot based on the first movement trajectory; and controlling the surgical robot to move based on the second movement trajectory.

In some embodiments, the controlling a target movement state of the surgical robot and/or the imaging device based on the initial movement state may include: controlling a movement speed of the surgical robot and/or the imaging device based on the initial movement state of the imaging device and/or the surgical robot.

In some embodiments, the method may further comprise: controlling the movement speed of the surgical robot and/or the imaging device based on the environmental information.

In some embodiments, the method may further comprise: obtaining a first end signal generated by the imaging device at an end of a current preset process, or a second end signal generated by the surgical robot at the end of the current preset process; and controlling a movement state of the imaging device and/or the surgical robot in a next process based on the first end signal or the second end signal.

In some embodiments, the controlling a movement state of the imaging device and/or the surgical robot in a next process based on the first end signal or the second end signal may include: controlling the imaging device to remain stationary, and/or be released from a stationary state of the surgical robot, based on the first end signal; and controlling the surgical robot to remain stationary, and/or be released from a stationary state of the imaging device, based on the second end signal.

In some embodiments, the method may further comprise: controlling, based on an access request from the surgical robot or the imaging device, the imaging device and the surgical robot to get into an integral working mode, wherein movement states of the imaging device and the surgical robot are mutually associated in the integral working mode.

In some embodiments, the method may further comprise: obtaining an interrupt request sent by the imaging device or the surgical robot; and controlling, based on the interrupt request, the imaging device and the surgical robot to get into an independent working mode, wherein the movement states of the imaging device and the surgical robot are independent of each other in the independent working mode.

In some embodiments, the method may further comprise: detecting a connection relationship between the imaging device and the surgical robot; and in response to the connection relationship being abnormal, controlling both the imaging device and the surgical robot to remain stationary.

In some embodiments, the method may further comprise: in response to a failure of the imaging device or the surgical robot, controlling the imaging device and the surgical robot to get into an independent working mode.

One of the embodiments of the present disclosure provides a system for controlling an image-guided interventional puncture device. The system may comprise: an imaging device, configured to obtain image data of a target object; and a surgical robot, configured to perform a puncture operation; and a control module, configured to control a target movement state of the surgical robot and/or the imaging device based on an initial movement state of the imaging device and/or the surgical robot.

In some embodiments, the system may further comprise: a display module, configured to receive control command information and movement status information output by the imaging device and/or the surgical robot and display the information in a display interface.

In some embodiments, the system may further comprise: a first interlock interface, configured to control the surgical robot to establish or interrupt a connection relationship with the imaging device, and to detect the connection relationship; a second interlock interface, configured to control a movement state of the imaging device based on a movement state of the surgical robot; and a third interlock interface, configured to control the imaging device and/or the surgical robot to remain stationary in a preset emergency situation.

In some embodiments, the system may further comprise: a first transmission channel, configured to transmit the image data obtained by the imaging device to the surgical robot to cause the surgical robot to perform the puncture operation based on the image data; and a second transmission channel, configured to transmit first movement state information of the imaging device to the surgical robot, and/or transmit second movement state information of the surgical robot to the imaging device.

One of the embodiments of the present disclosure provides a non-transitory computer readable storage medium, comprising at least one set of instructions, wherein when executed by at least one processor of a computer device, the at least one set of instructions directs the at least one processor to perform the method as mentioned above.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering denotes the same structure, wherein.

DETAILED DESCRIPTION

Figure 1:
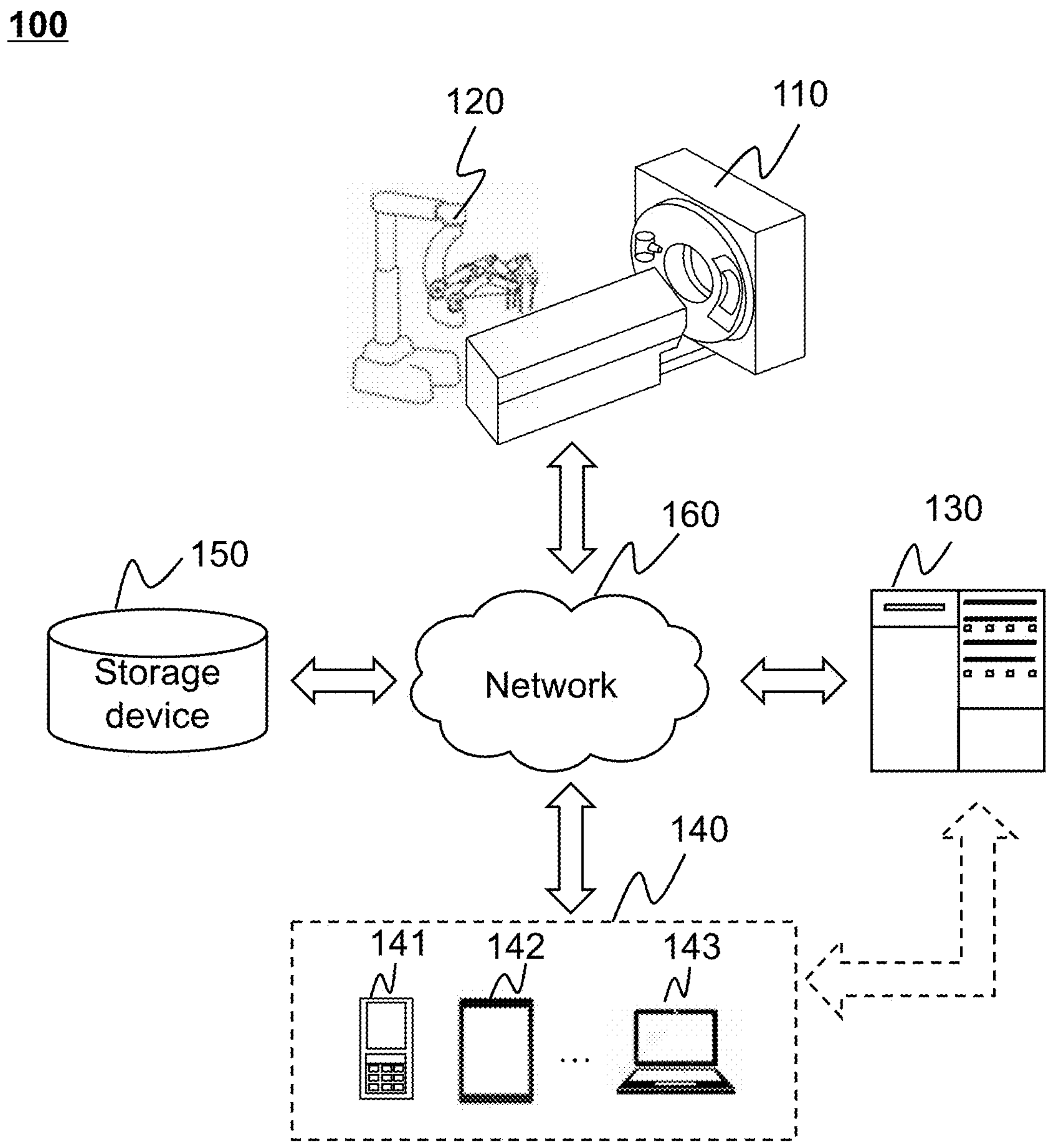
FIG. 1 is a schematic diagram illustrating an exemplary application scenario of an image-guided interventional puncture system according to some embodiments of the present disclosure.

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with the accompanying drawings without creative labor. Unless obviously obtained from the context or the context illustrates otherwise, the same numeral in the drawings refers to the same structure or operation.

It should be understood that as used herein, the terms “system”, “device”, “unit” and/or “module” are used herein as a way to distinguish between different components, elements, parts, sections, or assemblies at different levels. However, the words may be replaced by other expressions if other words accomplish the same purpose.

As shown in the present disclosure and the claims, unless the context clearly suggests an exception, the words “one,” “a”, “an”, “one kind”, and/or “the” do not refer specifically to the singular, but may also include the plural. Generally, the terms “including” and “comprising” suggest only the inclusion of clearly identified steps and elements that do not constitute an exclusive list, and the method or apparatus may also include other steps or elements.

Flowcharts are used in the present disclosure to illustrate operations performed by a system according to embodiments of the present disclosure. It should be appreciated that the preceding or following operations are not necessarily performed in an exact sequence. Instead, steps can be processed in reverse order or simultaneously. Also, it is possible to add other operations to these processes or remove a step or steps from them.

With the development of CT technology and surgical robots, CT imaging device-guided surgical robots are increasingly being used to assist physicians in performing puncture operations. Automatic needle insertion by surgical robots or physician-led surgical robots has become a major development trend in CT imaging device-guided interventional puncture surgery. Generally, products of CT imaging device-guided interventional surgical robots may be classified into two categories, miniaturized design products such as XACT, iSYS, etc., and surgical actuator arm design products such as MAXIO, ZeroBot, and so on. Miniaturized design products have a puncture device that is fixed directly to a scanning bed or bound to a patient, thus avoiding the risk of unintended relative movement between a surgical robot and a moving part of a CT imaging device. However, unintended movement due to patient misuse within the aperture of the CT imaging device may still occur, resulting in a puncture needle causing harm to the patient. Additionally, miniaturized design products are more limited in functionality due to their smaller size, making it difficult to meet most clinical puncture scenarios in terms of workspace. Puncture devices in the surgical actuator arm products have a large workspace, but unintended relative movement between the surgical actuator arm and the moving part of the CT imaging device is often difficult to avoid.

In some embodiments of the present disclosure, a method and system for controlling an image-guided interventional puncture device is provided, in which a movement state of one end of an imaging device or a surgical robot is controlled according to a movement state of another end of the imaging device or the surgical robot, which resolves the technical problem of possible unintended relative movement between the surgical robot and the CT imaging device, and improves the safety of the CT imaging device-guided surgical robot in completing a puncture action.

FIG. 1 is a schematic diagram illustrating an exemplary application scenario of an image-guided interventional puncture system according to some embodiments of the present disclosure.

In some embodiments, an image-guided interventional puncture system 100 may include an imaging device 110, a surgical robot 120, a processing device 130, a terminal device 140, a storage device 150, and a network 160, as shown in FIG. 1. In some embodiments, the processing device 130 may be a portion of the imaging device 110 and/or the surgical robot 120.

The imaging device 110 may scan a target object within a detection area or scanning area to obtain image data (e.g., a scanned image, etc.) of the target object. In some embodiments, the imaging device 110 may be a computed tomography (CT) scanner, a magnetic resonance imaging (MRI) scanner, a positron emission computed tomography (PET) scanner, a single photon emission computed tomography (SPECT), etc., or any combination thereof, for acquiring at least one of a CT image, an MR image, a PET image, a SPECT image or a combined image of the target object. The CT device may obtain scanned data according to the different absorption rates of different tissues of the human body for X-rays and the different transmission rates, and then input the scanned data into an electronic computer device to generate a cross-section or a three-dimensional image of the part to be examined. The MRI equipment may obtain the image data by examining hydrogen elements in the human body. The PET device may acquire the image data of a scanned object by means of a radioactive tracer. The SPECT device may acquire photons by means of a radioactive tracer and converts them into electrical signals to obtain the image data. It will be appreciated that the foregoing description relating to the imaging device is for illustrative purposes only and is not intended to limit the scope of the present disclosure.

The surgical robot 120 may be configured to perform an end operation (e.g., surgical actions such as ablation, puncture, suturing, etc.) on the target object. In some embodiments, the surgical robot 120 may include a surgical actuator arm structure with a fixation structure at an end of the surgical actuator arm for fixing surgical devices such as functional components (e.g., ablation needles, puncture needles, etc.). For more details, please see FIG. 6 (e.g., surgical robot 620) and its associated description, which will not be repeated here.

In some embodiments, the processing device 130 may direct the surgical robot 120 to perform a corresponding operation (e.g., a puncture operation) via remote control. In some embodiments, the processing device 130 may be electrically connected to a robotic arm end (e.g., a surgical actuator arm end 623) via a communication device (e.g., the network 160) for controlling the robotic arm end to drive a functional component (e.g., an ablation needle, a puncture needle, etc.) to perform a synchronized operation. For example, the processing device 130 may drive the puncture needle to perform a corresponding operation by controlling the robotic arm end to rotate, translate, or the like. For example, the processing device 130 may drive the puncture needle to perform a puncture operation by controlling the robotic arm end to advance forward. In some embodiments, the surgical robot 120 may be a robotic arm body for driving the robotic arm end in movement to control and/or adjust an operation and/or attitude (e.g., angle, position, etc.) of a functional component (e.g., the puncture needle) carried by the robotic arm end.

The processing device 130 may process data and/or information obtained from the imaging device 110, the surgical robot 120, the terminal device 140, the storage device 150, or other components of the image-guided interventional puncture system 100. For example, the processing device 130 may obtain a first movement state (e.g., in movement, be stationary, etc.) of the imaging device 110 and analyze and process the first movement state to determine a corresponding second movement state (e.g., in movement, be stationary, etc.) of the surgical robot 120 and/or a movement trajectory of the surgical robot 120. As another example, the processing device 130 may obtain a current image of the target object (e.g., a CT scanned image) from the imaging device 110 and analyze and process the current image to control the surgical robot 120 to guide the adjustment of the puncture needle. In some embodiments, the processing device 130 may be local or remote. For example, the processing device 130 may access information and/or data from the imaging device 110, the surgical robot 120, the terminal device 140, and/or the storage device 150 via the network 160.

In some embodiments, the processing device 130 and the imaging device 110 may be integrated. In some embodiments, the processing device 130 and the imaging device 110 may be directly or indirectly coupled to act jointly to implement the method and/or functions described herein.

In some embodiments, the processing device 130 and the surgical robot 120 may be integrated. In some embodiments, the processing device 130 and the surgical robot 120 may be directly or indirectly coupled to act in conjunction to realize the method and/or functions described herein. For example, the processing device 130 may be a control module in the surgical robot 120 shown in FIG. 7.

In some embodiments, the imaging device 110, the surgical robot 120, and the processing device 130 may be integrated into a single unit, such as an imaging device 610, a surgical robot 620, and a control module 630 in an image-guided interventional puncture system 600. In some embodiments, the imaging device 110, the surgical robot 120, and the processing device 130 may be directly or indirectly coupled to act in conjunction to realize the method and/or functions described herein, and more relevant content may be found in FIGS. 6 and 7 and descriptions thereof, and will not be repeated herein.

In some embodiments, the processing device 130 may include an input device and/or an output device. Interaction with a user (e.g., displaying information about the movement state of the imaging device 110 and/or the surgical robot 120, etc.) may be realized through the input device and/or the output device. In some embodiments, the input device and/or the output device may include a display, a keyboard, a mouse, a microphone, etc., or any combination thereof.

The terminal device 140 may be connected and/or in communication with the imaging device 110, the surgical robot 120, the processing device 130, and/or the storage device 150. For example, the terminal device 140 may obtain the current image of the target object from the imaging device 110 and display the current image, facilitating the user to monitor an actual puncture area of the puncture needle in real-time, etc. In some embodiments, the terminal device 140 may include a mobile device 141, a tablet 142, a laptop 143, etc., or any combination thereof. In some embodiments, the terminal device 140 (or all or part of its functionality) may be integrated in the imaging device 110 or the processing device 130.

The storage device 150 may store data, instructions, and/or any other information. In some embodiments, the storage device 150 may store data obtained from the imaging device 110, the surgical robot 120, and/or the processing device 130 (e.g., the current image of the target object, the movement state of the imaging device 110 and/or the surgical robot 120, the movement trajectory, a preset process, etc.). In some embodiments, the storage device 150 may store computer instructions for implementing a method for controlling an image-guided interventional puncture device.

In some embodiments, the storage device 150 may include one or more storage components, each of which may be a stand-alone device or may be part of other devices. In some embodiments, the storage device 150 may include random access memory (RAM), read-only memory (ROM), mass storage, removable memory, volatile read/write memory, etc., or any combination thereof. Exemplary mass storage may include disks, optical disks, solid-state disks, or the like. In some embodiments, the storage device 150 may be implemented on a cloud platform.

The network 160 may include any suitable network capable of facilitating the exchange of information and/or data, e.g., wireless network, wired network. In some embodiments, at least one component of the image-guided interventional puncture system 100 (e.g., the imaging device 110, the surgical robot 120, the processing device 130, the terminal device 140, the storage device 150) may exchange information and/or data with at least one other component of the system 100 via the network 160. For example, the processing device 130 may obtain a planning image and/or the current image of the target object from the imaging device 110 via the network 160.

It should be noted that the image-guided interventional puncture system 100 is provided for illustrative purposes only and is not intended to limit the scope of the present disclosure. For those of ordinary skill in the art, a wide variety of modifications or variations may be made in accordance with the description in the present disclosure. For example, the image-guided interventional puncture system 100 may be implemented on other devices with similar or different functionality. However, these changes and modifications do not depart from the scope of the present disclosure.

Figure 2:
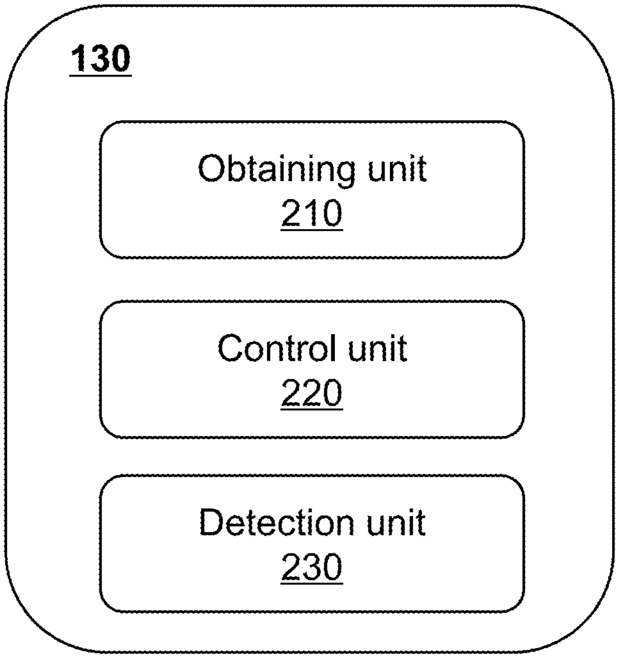
FIG. 2 is a schematic diagram illustrating exemplary modules of a processing device according to some embodiments of the present disclosure.

FIG. 2 is a schematic diagram illustrating exemplary modules of a processing device according to some embodiments of the present disclosure.

As shown in FIG. 2, in some embodiments, the processing device 130 may include an obtaining unit 210, a control unit 220, and a detection unit 230.

The obtaining unit 210 may be configured to obtain data and/or information related to components in an image-guided interventional puncture system. For example, the obtaining unit 210 may be configured to obtain a preset process, image data, or the like stored in the storage device 150. As another example, the obtaining unit 210 may be configured to acquire an access request, an interrupt request, an end signal, displacement data (e.g., a linear speed, an angular speed, etc., of various portions of a surgical robot), position data, a movement trajectory, etc., of an imaging device or the surgical robot.

In some embodiments, the obtaining unit 210 may be configured to obtain an initial movement state of an imaging device (e.g., imaging device 110) and/or a surgical robot (e.g., surgical robot 120). In some embodiments, the obtaining unit 210 may be configured to obtain a first end signal generated by the imaging device at an end of a current preset process, or a second end signal of the surgical robot at the end of the current preset process. In some embodiments, the obtaining unit 210 may be configured to obtain the access request, the interrupt request sent by the imaging device and/or the surgical robot. In some embodiments, the obtaining unit 210 may be configured to obtain environmental information.

Figure 3:
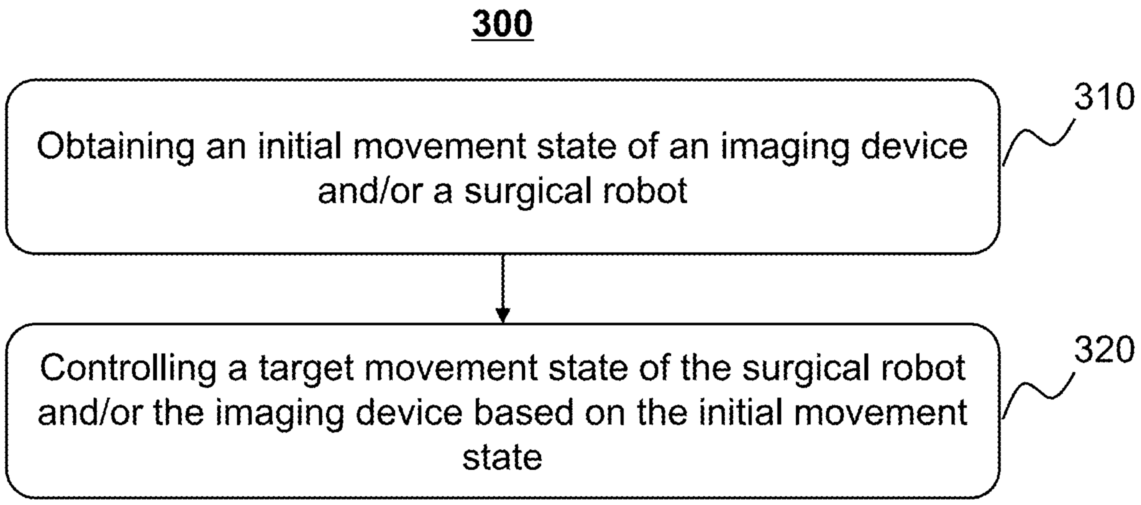
FIG. 3 is a flowchart illustrating an exemplary process for controlling an image-guided interventional puncture device according to some embodiments of the present disclosure.

For more information about the initial movement state, the preset process, the current preset process, the first end signal, and the second end signal, please see FIG. 3 and its related description. For more information about the image data, the access request, and the interrupt request, please see FIG. 4 and its related descriptions, which are not repeated here.

The control unit 220 may be configured to control components (e.g., the imaging device 110, the surgical robot 120, the terminal device 140) in an image-guided interventional puncture system (e.g., the image-guided interventional puncture system 100). For example, the control unit 220 may be configured to control the imaging device 110 to scan a target object to obtain image data of the target object, etc. As another example, the control unit 220 may be configured to control the surgical robot 120 to perform a puncture operation on the target object, etc.

In some embodiments, the control unit 220 may be configured to control a target movement state of the surgical robot and/or the imaging device based on an initial movement state of the imaging device and/or the surgical robot. In some embodiments, the control unit 220 may be configured to control a second movement state of the surgical robot based on the first movement state of the imaging device; and/or control, based on the second movement state of the surgical robot, the first movement state of the imaging device.

In some embodiments, the control unit 220 may be configured to control the surgical robot to remain stationary in response to a determination that the imaging device is in movement based on the first movement state of the imaging device; or to control the imaging device to remain stationary, based on the second movement state of the surgical robot, in response to a determination that the surgical robot is in movement. In some embodiments, the control unit 220 may be configured to determine a first movement trajectory of the imaging device based on the first movement state of the imaging device, and to control the surgical robot to move based on the first movement trajectory. In some embodiments, the control unit 220 may be configured to predict a distance between the imaging device and the surgical robot based on the first movement trajectory of the imaging device, and when the distance is less than a distance threshold, simultaneously control the imaging device and the surgical robot to remain stationary. In some embodiments, the control unit 220 may be configured to plan a second movement trajectory of the surgical robot based on the first movement trajectory, and to control the surgical robot to move based on the second movement trajectory.

In some embodiments, the control unit 220 may be configured to control a movement speed of the surgical robot and/or the imaging device based on the initial movement state of the imaging device and/or the surgical robot. In some embodiments, the control unit 220 may be configured to control the movement speed of the surgical robot and/or the imaging device based on the environmental information.

In some embodiments, the control unit 220 may be configured to control the imaging device and/or the surgical robot to proceed to a next process and/or the movement state of the imaging device and/or the surgical robot based on a first end signal or a second end signal. In some embodiments, the control unit 220 may be configured to control the imaging device to remain stationary and/or be released from a stationary state of the surgical robot based on the first end signal. In some embodiments, the control unit 220 may be configured to control the surgical robot to remain stationary, and/or be released from a stationary state of the imaging device based on the second end signal.

In some embodiments, the control unit 220 may be configured to control the imaging device and the surgical robot to get into an integral working mode in response to an access request from the surgical robot or the imaging device. In the integral working mode, movement states of the imaging device and the surgical robot are mutually associated. In some embodiments, the control unit 220 may be configured to control the imaging device and the surgical robot to get into an independent working mode based on an interrupt request or a fault detection result. In the independent working mode, the movement states of the imaging device and the surgical robot are independent of each other.

For more information about controlling the imaging device and/or the surgical robot, please see FIGS. 3-6 and their related descriptions.

The detection unit 230 may be configured to perform a fault detection on components in the image-guided interventional puncture system. For example, the detection unit 230 may be configured to perform a detection on the terminal device 140 to determine whether the terminal device properly displays a current image of the target object, etc. As another example, the detection unit 230 may be configured to perform a detection on the imaging device 110 to determine whether the imaging device 110 works normally, such as whether a scanning bed moves normally, whether the imaging device 110 scans the target object normally, etc.

In some embodiments, the detection unit 230 may be configured to detect the imaging device and the surgical robot separately, and when a fault of the device is detected, a detection signal is immediately generated and sent to the control unit 220. In some embodiments, the detection unit 230 may be configured to detect the connection relationship between the imaging device and the surgical robot, and when there is an abnormality in the connection relationship, generate a feedback signal and send the feedback signal to the control unit 220. The control unit 220 may be configured to control the imaging device and the surgical robot to get into the independent working mode or remain stationary at the same time in response to a fault of the imaging device or the surgical robot, or the abnormality in the connection relationship.

Specific qualifications regarding the processing device 130 can be found in the descriptions of the qualification of the process for controlling the device and will not be repeated herein. It will be appreciated that various units in the processing device 130 may be implemented, in whole or in part, by software, hardware, and combinations thereof. Each of the units may be embedded in or independent of the processing device 130 in the form of hardware, or may be stored in a memory in the processing device 130 in the form of software, so as to allow the processing device 130 to invoke the execution of individual modules corresponding to operations.

FIG. 3 is a flowchart illustrating a process for controlling an image-guided interventional puncture device according to some embodiments of the present disclosure. In some embodiments, a process 300 may be performed by the image-guided interventional puncture system 100 (e.g., the processing device 130). As shown in FIG. 3, the process 300 may include one or more of the following operations.

In 310, an initial movement state of an imaging device and/or a surgical robot may be obtained. In some embodiments, operation 310 may be performed by the obtaining unit 210.

The initial movement state may reflect a current movement state of the imaging device and/or the surgical robot. For example, the initial movement state may include that the imaging device or the surgical robot is in movement, and the imaging device or the surgical robot remains stationary. In some embodiments, the initial movement state may include movement data (e.g., a movement speed, a movement direction, a movement acceleration, etc.) of the imaging device or surgical robot. For example, the initial movement state may include data such as that the imaging device is moving at a speed of 1 cm/s at a constant speed, accelerating movement, decelerating movement, etc., and data such as linear speed, angular speed, etc., of various components of the surgical robot (e.g., a robotic arm, various joints, etc.).

In some embodiments, the initial movement state of the imaging device and/or the surgical robot may be obtained based on the movement state information fed back by the imaging device and/or the surgical robot. For example, the imaging device 110 may obtain information such as a current movement speed, position, etc., via a position sensor or a speed sensor, etc., generate first movement state information and transmit the first movement state information to the processing device 130. For example, the surgical robot 120 may obtain information about whether the surgical robot is currently in movement or is stationary by reading a preset process in a processor, generating second movement state information and transmitting the second movement state information to the processing device 130.

In 320, a target movement state of the surgical robot and/or the imaging device may be controlled based on the initial movement state. In some embodiments, operation 320 may be performed by the control unit 220.

The target movement state may refer to a movement state and/or a movement trajectory expected to be realized by the surgical robot and/or the imaging device. For example, the initial movement states of the imaging device and the surgical robot may be a stationary state and a movement state, respectively, and if the surgical robot has retreated to a preset altitude after completing the surgery, the surgical robot may be required to remain in the stationary state, then a scanning bed of the imaging device may begin to move to deliver a patient out of an aperture, then at this time, the target movement states of the surgical robot and the imaging device may be the stationary state and the movement state, respectively. The preset altitude may be an altitude set in advance.

In some embodiments, there are multiple implementations of controlling the target movement states of the surgical robot and/or the imaging device based on the initial movement state. For example, depending on the initial movement state, intelligent control via a preset process may be realized; or, for example, depending on the initial movement state, the control may be performed manually utilizing a human hand, and so forth. In some embodiments, a process of controlling the target movement states of the surgical robot and/or the imaging device and/or the surgical robot based on the initial movement states of the imaging device and/or the surgical robot may also be referred to as interlock control.

In some embodiments, controlling the target movement states of the surgical robot and/or the imaging device based on the initial movement states may include: controlling a second movement state of the surgical robot based on the first movement state of the imaging device; and/or controlling the first movement state of the imaging device based on the second movement state of the surgical robot. For example, the first movement state may include information such as whether the imaging device is currently in movement or stationary, a current linear speed, a historical linear speed, or the like. For example, the second movement state may include information such as the surgical robot is currently in movement or stationary, the angular speed and the linear speed of the surgical robotic arm, or the like.

The first movement state of the imaging device and the second movement state of the surgical robot may be determined in a variety of ways, such as manually, by mounted sensor detection, and so forth. In some embodiments, the first state of movement of the imaging device and the second state of movement of the surgical robot may be determined by a preset process of the system.

In some embodiments, the surgical robot may be controlled to remain stationary in response to a determination that the imaging device is in movement, based on the first movement state of the imaging device.

In some embodiments, the imaging device may be controlled to remain stationary in response to a determination that the surgical robot is in movement, based on the second movement state of the surgical robot.

In some embodiments, remaining stationary may include controlling a moving part of an imaging device or a surgical robot to be stationary, or locking the moving part. For example, a scanning bed of the imaging device may be locked while the surgical robot 120 is in movement. For example, the surgical actuator arm of the surgical robot 120 may be locked when the imaging device 110 is in movement. When the moving part is locked, its movement cannot be controlled even by operating a corresponding control button, and its movement may continue to be controlled only after it is unlocked.

In some embodiments, the surgical robot may be controlled to move based on movement information of the imaging device when the imaging device is in movement. For example, the processing device 130 may determine a real-time position of the imaging device based on displacement data of the imaging device 110, and when the imaging device is located in a target area or at a small distance from an edge of the target area, control the surgical robot to remain stationary or avoid the area. The target area may be an area where the surgical robot and the imaging device may collide. For example, the target area may be predicted based on historical movement data of the surgical robot and the imaging device.

In some embodiments, a first movement trajectory of the imaging device may be determined based on the first movement state of the imaging device, and the surgical robot may be controlled to move based on the first movement trajectory.

The first movement trajectory may be a movement path of the imaging device over a period of time in a three-dimensional space. For example, prior to performing a puncture surgery, a target object is transported into an aperture of a gantry by the scanning bed of the imaging device to be scanned, and at this time, the first movement trajectory of the imaging device is a movement path of the scanning bed from a current position into the aperture. A trajectory shape of the first movement trajectory is not limited, and may be a straight line or other shapes such as an arc.

Depending on the first movement state of the imaging device, the first movement trajectory of the imaging device may be determined utilizing a variety of means. For example, the first movement trajectory of the imaging device may be determined by establishing a three-dimensional spatial coordinate system and determining information such as the movement speed, position, or the like of the imaging device based on the first movement state of the imaging device. In some embodiments, the first movement trajectory of the imaging device may be obtained directly from the imaging device.

In some embodiments, a distance between the imaging device and the surgical robot may be predicted based on the first movement trajectory of the imaging device, and when the distance is less than a distance threshold, the imaging device and the surgical robot may be simultaneously controlled to remain stationary. For example, when the distance is less than the distance threshold, the moving parts of the imaging device and the surgical robot may be simultaneously controlled to remain stationary, or the moving parts of the imaging device and the surgical robot may be locked. The distance threshold refers to a minimum value of distance that may be allowed.

Depending on the first movement trajectory of the imaging device, the distance between the imaging device and the surgical robot may be predicted using a variety of ways, including but not limited to program algorithms. For example, the processing device 130 may determine the current position (e.g., three-dimensional spatial coordinates) of the imaging device based on the first movement trajectory, and utilize a program algorithm to calculate, based on a current movement speed, a position of the imaging device at a next moment, compare that position to a position of the surgical robot, and determine the distance between the imaging device and the surgical robot.

In some embodiments, the distance between the imaging device and the surgical robot may be obtained by a sensor. For example, an infrared sensor, a laser sensor, an ultrasonic sensor, or the like may be mounted on the surgical robot to obtain the distance between the imaging device and the surgical robot. In some embodiments, an installation position and/or type of the sensor may be set according to actual needs, for example, to be installed on the gantry of the imaging device, on a side edge of the scanning bed, etc., which is not limited in the present disclosure.

If the distance between the imaging device and the surgical robot is less than the distance threshold, simultaneously controlling the moving parts of the imaging device and the surgical robot to remain stationary or locking the moving parts can prevent the two from colliding to cause damage to the device and protect the target object's safety.

In some embodiments, a second movement trajectory of the surgical robot may be planned based on the first movement trajectory; and based on the second movement trajectory, the surgical robot may be controlled to move.

The second movement trajectory may refer to a movement path of the surgical robot over a period of time in a three-dimensional space. For example, after the imaging device completes scanning the target object, the surgical robot may perform a local anesthesia operation, and at this time, the surgical robot needs to move from the current position to an operable region, then a path from the current position to the operable region may be considered as the second movement trajectory of the surgical robot. A shape of the second movement trajectory may be various, such as a straight line, an arc, and so on. The operable region refers to a region in which the surgical robot may realize a relevant surgical operation.

In some embodiments, a movement position of the imaging device at each moment may be determined based on the first movement trajectory, and the second movement trajectory of the surgical robot may be planned based on the movement position to avoid collision of the surgical robot with the imaging device. For example, the processing device 130 may determine spatial coordinates of the imaging device at different moments based on the first movement trajectory, plan the movement position of the surgical robot based on the spatial coordinates, so that the distance between the surgical robot and the imaging device is greater than a preset value to determine the second movement trajectory of the surgical robot.

In some embodiments, the movement speed of the surgical robot and/or the imaging device may be controlled based on the initial movement states of the imaging device and/or the surgical robot.

In some embodiments, a real-time distance between the imaging device and the surgical robot may be determined based on the first movement state of the imaging device and the second movement state of the surgical robot, and when the distance is greater than a preset threshold (e.g., 1 meter or 2 meters), the surgical robot or the imaging device may be controlled to move at a first speed; when the distance is less than or equal to the preset threshold, the surgical robot or the imaging device may be controlled to move at a second speed, and the first speed is greater than the second speed. For example, when the imaging device 110 remains stationary, the processing device 130 may determine a real-time position of the surgical robot 120 based on the second movement state of the surgical robot 120, and determine the distance between the surgical robot 120 and the imagining device 110 based on the position of the imaging device 110 and the position of the surgical robot 120. As another example, when the imaging device 110 and the surgical robot 120 are in movement at the same time, the processing device 130 may determine a first position of the imaging device 110 based on the first movement state, determine a second position of the surgical robot 120 based on the second movement state, and determine the distance between the two based on the first position and the second position at the same moment. In some embodiments, the real-time distance between the two may be determined by a sensor, which is not limited in the present disclosure. For example, the real-time distance between the two may be determined by a radar sensor mounted on the imaging device 110 or the surgical robot 120.

The control of a magnitude of the movement speed of the surgical robot and/or the imaging device may be the same or different, depending on the circumstances.

In some embodiments, the movement speeds of the surgical robot and/or the imaging device may be controlled based on environmental information.

The environmental information refers to information related to an area in which the imaging device and the surgical robot are located. For example, the environmental information may be information about a location of the surgical robot and the imaging device, information such as movement information (e.g., body movement, hand lifting, etc.) of the target object, or any object (e.g., a person, other device, etc.) contained in a surrounding area of the device.

The environmental information may be acquired in a variety of ways. For example, the environmental information may be acquired by a sensor, by a camera device, etc., which is not limited in the present disclosure.

In some embodiments, depending on the environmental information, the movement speed of the surgical robot and/or the imaging device may be controlled by manual speed regulation, programmed automatic speed regulation, or the like. For example, when the surgical robot is moving toward the target object, the target object suddenly raises its hand so that the hand is close to the surgical robot, and at this time, the program may control the surgical robot to reduce the speed to avoid collision causing injury to the target object. When the target object's hand is put back to an original position, the program may control the surgical robot to return to an original speed, thereby saving running time and improving surgical efficiency. In some embodiments, when the surgical robot stops moving and the distance between the imaging device and the surgical robot is still decreasing, the imaging device may be controlled to stop moving at the same time. In some embodiments, when the surgical robot stops moving and the distance between the imaging device and the surgical robot is still decreasing, the imaging device may be controlled to stop moving at the same time.

In some embodiments, a first end signal generated by the imaging device at an end of a current preset process or a second end signal generated by the surgical robot at the end of the current preset process may be obtained; the movement states of the imaging device and/or the surgical robot may be controlled based on the first end signal or the second end signal to get into a next process.

The preset process is a work task process pre-set by the system. For example, a complete preset process may be: scanning→local anesthesia puncture→delivering the patient to the aperture→puncture→removing the patient out of the aperture→end, wherein the scanning, delivering the patient to the aperture, removing the patient out of the aperture need to be performed by the imaging device, and the local anesthesia puncture and puncture need to be executed by the surgical robot. The current preset process may refer to preset process information corresponding to this current stage, such as process information of scanning the target object, performing the puncture surgery on the target object, and so on. In some embodiments, the system may automatically determine a corresponding preset process based on patient information, or a physician may manually set the current preset process for the target object.

The first end signal may refer to a feedback signal generated when the imaging device completes the current preset process. For example, the first end signal may be generated after the imaging device 110 controls the scanning bed to deliver the target object within the aperture of the gantry. As another example, after the imaging device 110 completes scanning the target object, the first end signal may be generated.

The second end signal may refer to a feedback signal generated when the surgical robot completes the current preset process. For example, the second end signal may be generated after the surgical robot 120 completes the local anesthetic puncture of the target object. As another example, after the surgical robot 120 completes the puncture surgery on the target object, the second end signal may be generated.

The first end signal and the second end signal may be expressed in a variety of ways. For example, the imaging device and the surgical robot may reflect that the imaging device and the surgical robot have completed the current preset process by means of a warning tone, an indicator light, or the like. In some embodiments, the first end signal and the second end signal may be code information generated in the processing device. In some embodiments, the first end signal and the second end signal may include execution content of the current preset process. For example, the first end signal may be displayed in a display interface in the form of a pop-up window, such as "the target object has been delivered to the aperture".

In some embodiments, the imaging device and/or the surgical robot may send the first end signal or the second end signal via a data transmission channel. For example, the imaging device 110 or the surgical robot 120 may transmit the first end signal or the second end signal via a second transmission channel, and more details of the second transmission channel may be found in FIG. 7 and descriptions thereof.

The next process refers to a work task corresponding to a next stage after completing the current preset process. For example, after the imaging device finishes scanning the target object, the next process may be for the surgical robot to perform local anesthesia puncture on the target object, etc.

In some embodiments, the imaging device may be controlled to remain stationary (e.g., controlling the moving parts of the imaging device to enter a locked state), and/or be released from the stationary state of the surgical robot (e.g., releasing locking of the moving parts of the surgical robot), based on the first end signal. In some embodiments, the surgical robot may be controlled to remain stationary, and/or release the stationary state of the imaging device, based on the second end signal. For example, the first end signal is generated when the imaging device 110 ends scanning of the target object, and based on the first end signal, the control unit 220 may control the scanning bed of the imaging device 110 to enter a locked state and to unlock the moving parts of the surgical robot 120 so that the surgical robot may complete the local anesthesia operation. As a further example, the second end signal is generated when the surgical robot 120 completes the puncture surgery and is returned to the original position, and according to the second end signal, the control unit 220 may control the moving parts of the surgical robot 120 to enter the locking state and unlock the scanning bed of the imaging device 110 to enable the scanning bed of the imaging device 110 to move the target object out of the aperture of the gantry.

In some embodiments, the surgical robot may be controlled to move based on patient information. For example, different displacements are preset for the surgical actuator arm for different body types (e.g., larger displacements for those with more fat, etc.), and when performing the puncture surgery, a body type of a current target object is obtained, and the surgical actuator arm is controlled to move according to a preset correspondence in order to perform the puncture surgery on the target object.

In some embodiments, the imaging device may be controlled to get into an integral working mode with the surgical robot in response to an access request from the surgical robot or the imaging device. In response to getting into the integral working mode, the target movement states of the surgical robot and/or the imaging device may be controlled based on the initial movement states of the imaging device and/or the surgical robot. In some embodiments, the imaging device and the surgical robot may be controlled to get into an independent working mode based on an interrupt request. Details of the integral working mode and the independent working mode can be found in FIG. 4 and its related descriptions and will not be repeated here.

By controlling the movement state of the surgical robot based on the movement state of the imaging device and controlling the movement state of the imaging device based on the movement state of the surgical robot, the unintended relative movement of the imaging equipment and the surgical robot can be effectively solved to avoid equipment damage and injury to the patient. By means of the end signal, the movement states of the imaging device and the surgical robot are controlled after completion of the current preset process, so as to ensure that interlocked control of the movement states is realized when the preset process is switched and to avoid unintended relative movement, further reducing the risk of the image-guided interventional puncture system. By controlling the movement speeds of the surgical robot and/or the imaging device based on the initial movement states of the imaging device and/or the surgical robot and the environmental information, the device can be prevented from collision resulting in damage, and the running time of the device can be effectively saved, the progress of the surgery can be accelerated, and the efficiency of the surgery can be improved.

Figure 4:
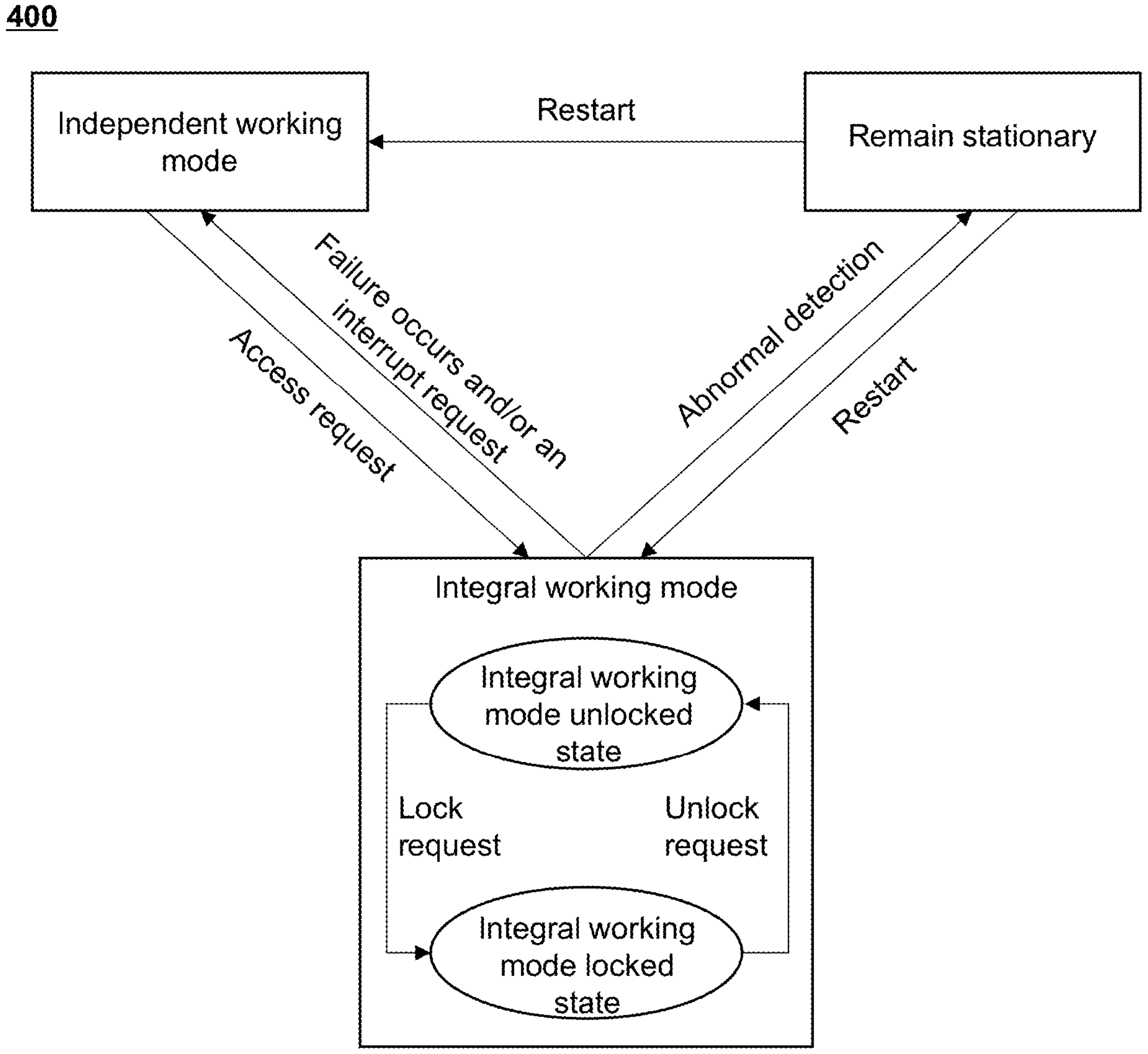
FIG. 4 is a schematic diagram illustrating an exemplary working mode of the image-guided interventional puncture system according to some embodiments of the present disclosure.

FIG. 4 is a schematic diagram illustrating an exemplary working mode of an image-guided interventional puncture system according to some embodiments of the present disclosure.

As shown in FIG. 4, in some embodiments, an image-guided interventional puncture system 400 may include an integral working mode and an independent working mode, in which switching between the working modes is possible via a connection interface (e.g., a first interlock interface). More information about the connection interface can be found in FIG. 6 and its related descriptions, which will not be repeated here.

In the integral working mode, movement states of the imaging device and the surgical robot are mutually associated. In the independent working mode, the movement states of the imaging device and the surgical robot may be independent of each other without interlocking control. For example, in the integral working mode, the surgical robot enters a locking state when the imaging device is in movement, and the imaging device enters a locking state when the surgical robot is in movement; in the independent working mode, the connection between the imaging device and the surgical robot is disconnected, and the movement of the two is unaffected by each other.

In some embodiments, the imaging device or the surgical robot may send an access request to a controller (e.g., the processing device 130, the control module 630), and the controller may establish a connection relationship between the imaging device and the surgical robot based on the access request in order to control the imaging device and the surgical robot to get into the integral working mode. The access request may be an instruction signal from the surgical robot or imaging device requesting access. For example, after receiving a first access request from an imaging device 610 or a second access request from a surgical robot 620, a control module 630 may establish a connection relationship with the imaging device 610 and the surgical robot 620, respectively, and the control module 630 may be used as an intermediary for data transmission, thereby establishing a connection relationship between the imaging device 610 and the surgical robot 620. The connection relationship between the imaging device and the surgical robot is established through the controller to facilitate the direct transmission of a control signal to directly control the movement state of the imaging device and the surgical robot without the need to establish a connection channel each time the interlocking control is performed, which improves the execution efficiency of the image-guided interventional puncture system.

In some embodiments, the imaging device may send the first access request to the surgical robot, and after the surgical robot accepts the first access request, the surgical robot and the imaging device may get into the integral working mode. In some embodiments, the surgical robot may send the second access request to the imaging device, and after the imaging device accepts the second access request, the surgical robot and the imaging device may get into the integral working mode. For example, the imaging device or the surgical robot may send the first access request or the second access request during a preparation phase of the image-guided interventional puncture system.

In some embodiments, the first access request or the second access request may be generated in response to a user operation. For example, a user may connect a communication cable of the imaging device 110 to an interface board of the controller of the surgical robot 120, and the imaging device 110 may detect that the communication cable is connected and generate the first access request. For example, after the imaging device 110 is connected to the surgical robot 120 via a hardware connection, the surgical robot 120 may generate the second access request in response to an operation that switches a working mode of the surgical robot 120 by the user. In such a case, after the imaging device 110 and the surgical robot 120 are connected via the hardware connection, the imaging device 110 may remain in the independent working mode. In some embodiments, the first access request or the second access request may be generated based on a preset condition. For example, after the imaging device 110 and the surgical robot 120 are connected via hardware, the access request may be generated by the imaging device 110 or the surgical robot 120 when a length of the connection reaches a preset time threshold.

When the imaging device and the surgical robot get into the integral working mode, the surgical robot may be guided by the imaging device to perform the puncture operation, thereby performing the puncture operation under the integral working model. In some embodiments, the execution may be performed with interlocking controls that enable locking control of the surgical robot while the imaging device is scanning (e.g., controlling moving parts of the surgical robot to remain stationary or locked), and locking control of the imaging device while the surgical robot is performing the puncture operation (e.g., controlling moving parts of the imaging device to remain stationary or locked). In some embodiments, the moving parts of the imaging device or the surgical robot may be controlled based on a preset process, or a movement state of the imaging device/surgical robot. For example, the processing device 130 may lock the moving parts of the surgical robot 120 when the imaging device 110 is in movement. For example, when the imaging device 110 ends the current preset process, the processing device 130 may control the imaging device 110 to remain stationary and/or lock the moving parts thereof, while unlocking the moving parts of the surgical robot 120.

In some embodiments, the imaging device or the surgical robot may send the interrupt request (e.g., a first interrupt request, a second interrupt request) to the controller (e.g., the processing device 130, the control module 630), and the controller may interrupt the connection relationship between the imaging device and the surgical robot based on the interrupt request in order to control the imaging device and the surgical robot to get into the independent working mode. The interrupt request may refer to an instruction signal from the surgical robot or imaging device requesting an interrupt. In some embodiments, the interrupt request may include a third-party instruction, such as an operating instruction entered by the user, etc.

Exemplarily, when the imaging device 610 needs to exit the integral working mode, the first interrupt request may be sent to the control module 630, and the control module 630, upon receiving the first interrupt request, may interrupt the connection relationship between the imaging device 610 and the surgical robot 620. For example, the control module 630 may interrupt the connection channel with the imaging device 610 and the surgical robot 620, respectively, thereby interrupting the connection relationship between the imaging device 610 and the surgical robot 620.

Exemplarily, when the surgical robot 620 needs to exit the integral working mode, the second interrupt request may be sent by the surgical robot 620 to the control module 630, and the control module 630 may receive the second interrupt request to interrupt the connection relationship between the surgical robot 620 and the imaging device 610.

In some embodiments, the imaging device may send the first interrupt request to the surgical robot (e.g., after an interventional guided operation ends), and the surgical robot may accept the first interrupt request and break the connection relationship, and the surgical robot and the imaging device may get into the independent working mode. In some embodiments, the surgical robot may send the second interrupt request to the imaging device, and the imaging device may receive the second interrupt request and interrupt the connection relationship, and the surgical robot and the imaging device may get into the independent working mode.

In the independent working mode, the surgical robot is evacuated and the imaging device may be used alone to perform a scanning operation (e.g., clinical imaging scanning).

The image-guided interventional puncture system may be improved by interrupting the connection relationship between the imaging device and the surgical robot, thereby ensuring that the surgical robot may be evacuated in a timely manner at an end of the surgery, and ensuring that the imaging device works independently without affecting a normal operation of the system, henceforth improving the efficiency and experience of using the system.

In some embodiments, the imaging device and the surgical robot may be controlled to enter a failure mode when the connection relationship between the imaging device and the surgical robot is abnormal. For example, the failure mode may include simultaneously controlling the moving parts of the imaging device and the surgical robot to remain stationary and/or locking the moving parts of the imaging device and the surgical robot.

In some embodiments, after getting into the integral working mode, the connection relationship between the imaging device and the surgical robot may be detected; when the connection relationship is abnormal, the imaging device and the surgical robot may be simultaneously controlled to remain stationary. The connection relationship may be a hardware connection relationship or a software connection relationship. If an abnormal condition is detected in the connection relationship, it indicates that there may be a failure in the system, and that continuing to perform the surgical surgery may lead to a dangerous condition. Therefore, it is necessary to send a control signal to the imaging device and to the surgical robot at the same time, and to control the imaging device and the surgical robot to end the movement states, so as to avoid harm to the patient.

For example, in the integral working mode, the control module 630 may detect a working state of the hardware interface and the software interface of the imaging device 610 and the surgical robot 620, and when an abnormal condition exists in an interface cable or software, the control module 630 may generate the control signal and send the control signal to the imaging device 610 and the surgical robot 620 to control the imaging device 610 and the surgical robot 620 to get into a locked state. In some embodiments, the surgical robot or the imaging device may self-repair after getting into the locked state. If the self-repair fails, manual inspection and repair may be performed. After the repair is completed, restarting the imaging device and the surgical robot, and the imaging device and the surgical robot may directly get into the internal working mode or the independent working mode, or may get into the integral working mode or the independent working mode based on the access request or interruption request of the imaging device or the surgical robot, which can be set by the user.

In some embodiments, it is possible to control the imaging device and the surgical robot to get into the failure mode in response to a determination that there is an unintended movement of the target object. For example, an image of a patient may be captured in real-time by a camera, and when the presence of unintended movement of the patient is recognized based on a captured image (a preset standard posture is to lie flat with hands on either side of the legs, but the patient's hands are raised or placed at the site of the puncture), the imaging device and the surgical robot may be controlled to remain stationary at the same time.

In some embodiments, the control module may also control the imaging device and the surgical robot to get into the independent working mode in response to a failure of the imaging device or the surgical robot. The failure may include an abnormality in the connection relationship between the imaging device and the surgical robot, the surgical robot or the imaging device going down, etc. For example, in the integral working mode, if the surgical robot 120 fails, the control module, after detecting the failure thereof, may generate the control signal and send the control signal to the imaging device 110 and the surgical robot 120 to control the imaging device 110 and the surgical robot 120 to forcibly disconnect and get into the independent working mode, at which time, the imaging device 110 may independently perform a scanning operation.

The safety of the image-guided interventional puncture system may be improved by detecting the connection relationship between the imaging device and the surgical robot and locking the moving parts of the imaging device and the surgical robot when the connection relationship is abnormal, thus avoiding unintended relative movement and avoiding the impact of unexpected events on the image-guided interventional puncture system, henceforth improving the safety of the image-guided interventional puncture system.

Figure 5:
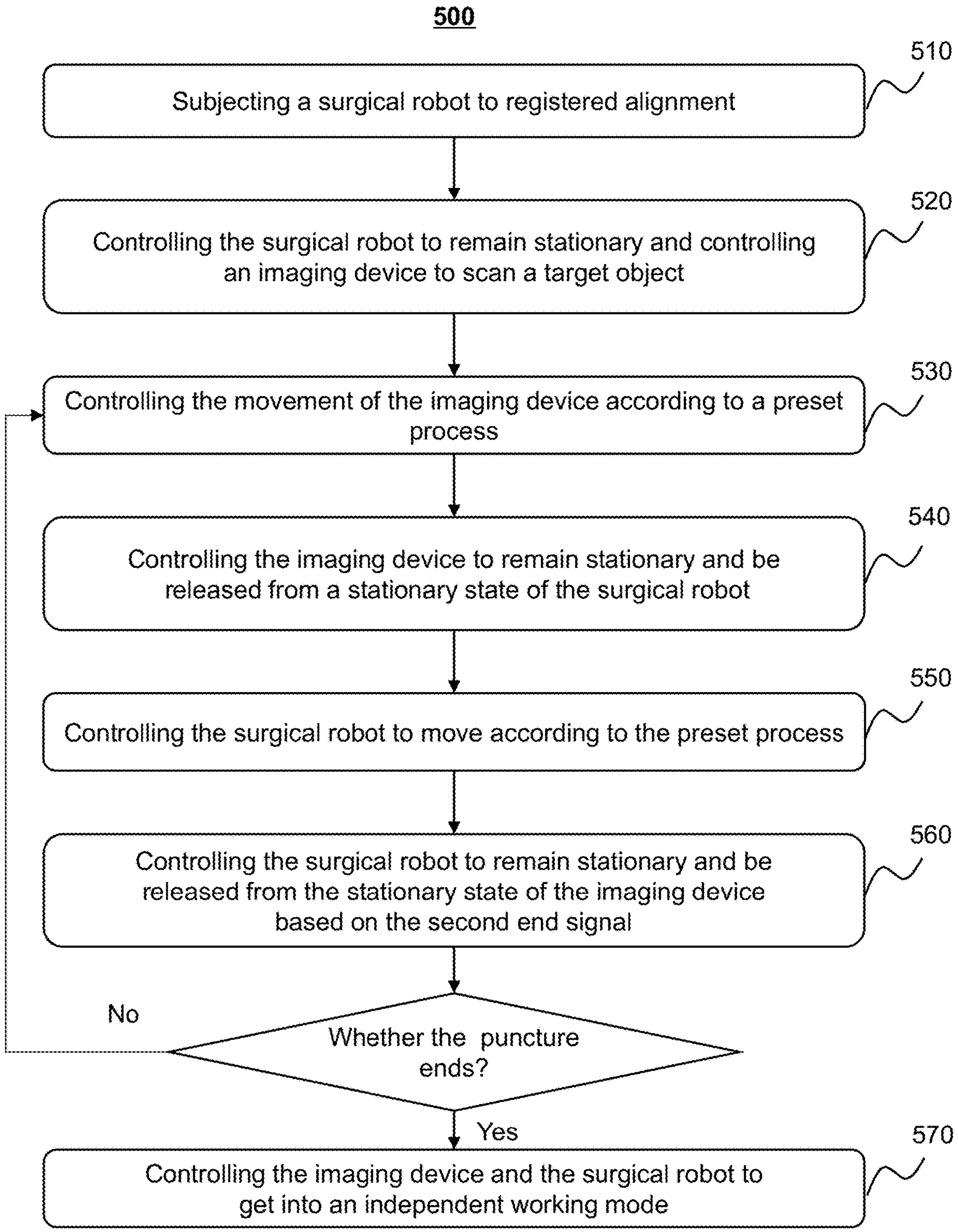
FIG. 5 is a flowchart illustrating an exemplary process for controlling the image-guided interventional puncture device according to another embodiment of the present disclosure.

FIG. 5 is a flowchart illustrating an exemplary process for controlling an image-guided interventional puncture device according to another embodiment of the present disclosure. In some embodiments, a process 500 may be performed by the image-guided interventional puncture system 100 (e.g., the processing device 130). As illustrated in FIG. 5, the process 500 may include one or more of the following operations.

In 510, a surgical robot may be subjected to registered alignment. In some embodiments, operation 510 may be performed by the processing device 130.

The registered alignment refers to matching a 3D space of a target object with a 3D space of a scanned image to unify them under the same coordinate system.

For example, after an imaging device and the surgical robot get into an integral working mode, three-dimensional coordinates or a scanned image of a patient may be associated under a unified coordinate system through the registered alignment, so as to realize the transformation of the three-dimensional spatial coordinates or coordinates of the scanned image and the coordinates of the surgical robot to determine a surgical position and establish a connection channel.

In 520, the surgical robot may be controlled to remain stationary, and the imaging device may be controlled to scan the target object. In some embodiments, operation 520 may be performed by the processing device 130.

In some embodiments, upon completion of the registered alignment, the surgical robot may generate a second end signal and send the second end signal to a controller (e.g., the processing device 130). After receiving the second end signal, the controller may control the surgical robot to remain stationary and control the imaging device to scan the target object. For example, the processing device 130 may lock a surgical actuator arm of the surgical robot 120 based on the second end signal and control the imaging device 110 to scan the target object to obtain a scanned image. As another example, the processing device 130 may control the surgical robot 120 to move to a target position (e.g., a position that does not interfere with the movement of the imaging device) and then come to rest and lock the surgical actuator arm based on the second end signal. The imaging device 110 may be then controlled to scan the target object to obtain the scanned image of the target object.

In 530, the movement of the imaging device may be controlled according to a preset process. In some embodiments, operation 530 may be performed by the processing device 130.

In some embodiments, the processing device 130 may control the imaging device to move or remain stationary, depending on the preset process. For example, when the preset process includes local anesthesia puncture, after the imaging device 110 completes the scanning, the imaging device 110 may generate a first end signal and send the first end signal to the processing device 130, and the processing device 130, after receiving the first end signal, may lock a scanning bed of the imaging device 110 and control the surgical robot 120 to get into a workflow (i.e., local anesthesia puncture), to enable the surgical actuator arm to perform the local anesthesia puncture on the patient; after completing this workflow, the surgical robot 120 may generate the second end signal and send the second end signal to the processing device 130, which unlocks the scanning bed according to the second end signal and controls the imaging device 110 to get into a workflow (i.e., deliver the patient into an aperture), to enable the imaging device 110 to transport the patient through the scanning bed into an aperture of a gantry. As another example, when the preset process does not include the local anesthesia puncture, the processing device 130 may control, according to the preset process, when the imaging device 110 has completed the scanning, the imaging device 110 to transport the target object through the scanning bed to the aperture of the gantry and position a puncture level.

In 540, based on the first end signal, the imaging device may be controlled to remain stationary and be released from a stationary state of the surgical robot. In some embodiments, operation 540 may be performed by the processing device 130.

In some embodiments, upon completing positioning the puncture level, the imaging device may generate the first end signal and send the first end signal to the controller (e.g., the processing device 130), which may control moving parts of the imaging device (e.g., the scanning bed) to remain stationary and/or to get into a locked state based on the first end signal, and unlock moving parts of the surgical robot from a locked state or the stationary state. For example, the processing device 130 may lock the scanning bed and a gantry of the imaging device 110 and unlock the surgical actuator arm of the surgical robot 120 to allow the surgical actuator arm to move into the aperture of the gantry and perform a puncture operation on the patient, based on a received end signal.

In 550, the surgical robot may be controlled to move according to the preset process. In some embodiments, operation 550 may be performed by the processing device 130.

In some embodiments, the processing device 130 may send a control signal to the surgical robot according to the preset process, and the surgical robot may control the surgical actuator arm to move after receiving the control signal, so as to cause the surgical actuator arm to enter into the aperture of the gantry to perform a master-slave puncture action on the target object. Further, after completing the master-slave puncture action, the surgical robot may control the surgical actuator arm to move out of the aperture of the gantry according to a control instruction.

In 560, based on the second end signal, the surgical robot may be controlled to remain stationary and be released from the stationary state of the imaging device. In some embodiments, operation 560 may be performed by the processing device 130.

In some embodiments, after the surgical actuator arm has moved out of the aperture of the gantry, the surgical robot may generate the second end signal and send the second end signal to the controller (e.g., the processing device 130), which may control, based on the second end signal, the moving parts of the surgical robot (e.g., the surgical actuator arm) to remain stationary or to get into the locked state, and release the stationary state or the locked state of the moving parts of the imaging device. For example, the processing device 130 may lock, based on the second end signal, the surgical actuator arm and unlock the scanning bed in order to allow the imaging device 110 to get into a workflow (i.e., remove the patient out of the aperture), wherein the imaging device 110 moves the patient out of the aperture of the gantry through the scanning bed.

Further, the processing device 130 may determine whether the puncture surgery is over, and if the puncture surgery is over, the process may proceed to operation 570; otherwise, the process may proceed to operation 530 (i.e., controlling the movement of the imaging device according to the preset process (e.g., controlling the movement of the imaging device according to a next workflow)). In some embodiments, it is possible to determine whether the puncture surgery is over based on the preset process. In some embodiments, it can be determined whether the puncture surgery is over based on an end signal. For example, an end of the puncture surgery may be determined based on a "patient has been moved out of the aperture" signal sent by the imaging device 110.

In 570, the imaging device and the surgical robot may be controlled to get into an independent working mode. In some embodiments, operation 570 may be performed by the processing device 130.

In some embodiments, in response to a determination that the puncture surgery has been completed, the processing device 130 may unlock the imaging device (e.g., the scanning bed) and/or the surgical robot (e.g., the surgical actuator arm) and interrupt a connection relationship between the imaging device and the surgical robot in order to allow the imaging device and the surgical robot to get into the independent working mode.

Through the first end signal and the second end signal, movement states of the imaging device and the surgical robot are controlled after completing the preset process, so as to ensure that interlocked control of the movement states is realized during the switching of the preset process and avoid unintended relative movement, which can further reduce the risk of the image-guided interventional puncture system.

Figure 6:
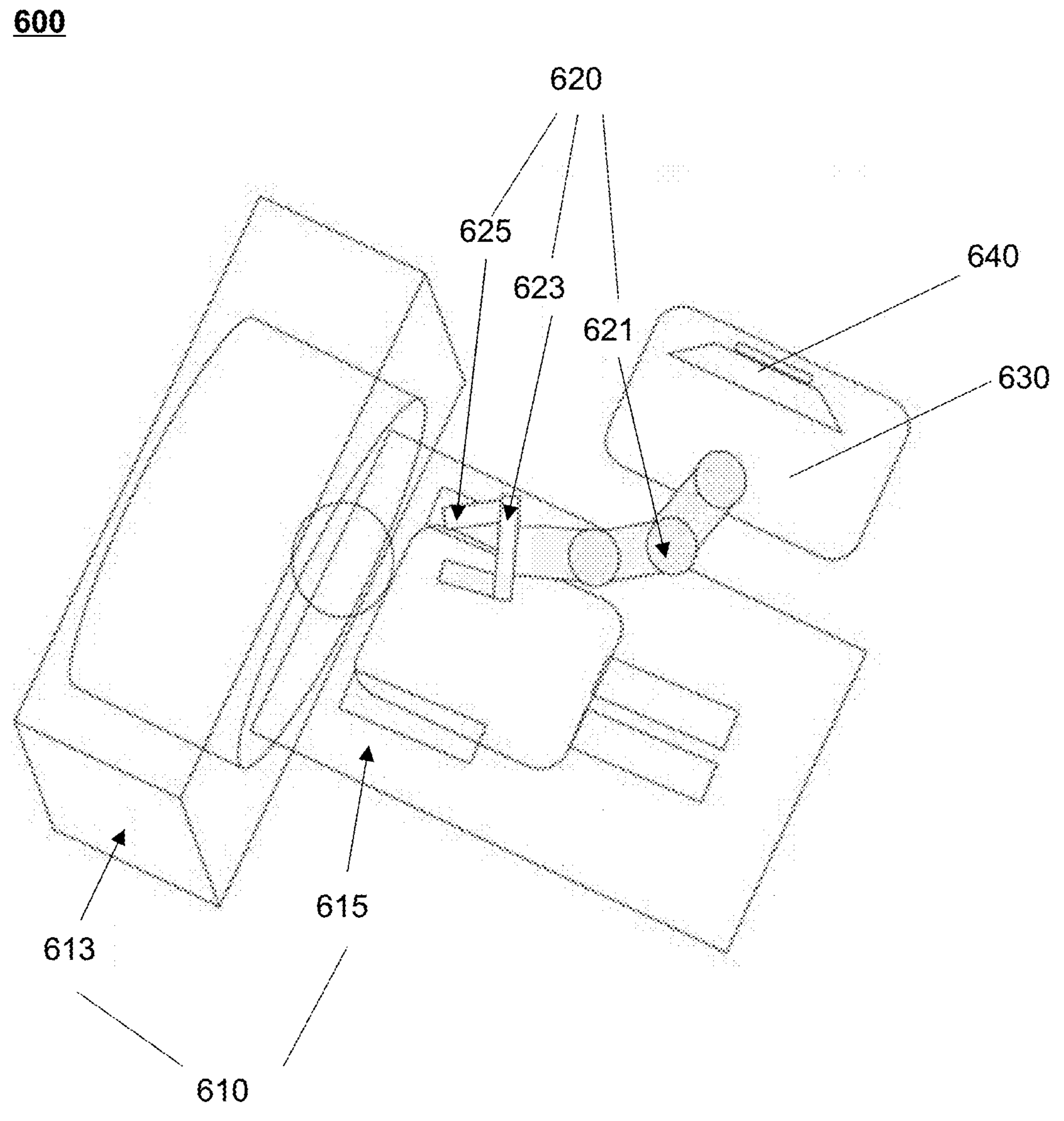
FIG. 6 is a schematic diagram illustrating an exemplary structure of the image-guided interventional puncture system according to some embodiments of the present disclosure.

FIG. 6 is a schematic diagram illustrating an exemplary structure of an image-guided interventional puncture system according to some embodiments of the present disclosure.

As shown in FIG. 6, in some embodiments, the image-guided interventional puncture system 600 may include the imaging device 610, the surgical robot 620, and the control module 630. Wherein the imaging device 610, the surgical robot 620, and the control module 630 are structures or components similar to the imaging device 110, the surgical robot 120, and the processing device 130 of the image-guided interventional puncture system 100, respectively. In some embodiments, the control module 630 may be integrated into the surgical robot 620 and communicatively connected to the imaging device 610 for controlling the imaging device 610 as well as the surgical robot 620.

In some embodiments, the imaging device 610 may include a gantry 613 and a scanning bed 615. Taking the imaging device 610 as an example of a CT device, in some embodiments, the gantry 613 may be equipped with an X-ray bulb tube, a filter, a collimator, a reference detector, a signal detector, electronic circuits, and various moving parts. In some embodiments, movement parts of the gantry 613 may control the gantry to perform movement such as linear movement, rotational movement, forward and backward tilting movement, or the like. In some embodiments, a distance between the X-ray bulb tube and a target object may be changed based on the moving parts, as well as adjusting a tilt angle of the gantry 613, which may be ±20°~±30°. The scanning bed 615 is a carrier of the target object. In some embodiments, the scanning bed 615 has a vertical movement part and a horizontal longitudinal movement part, which is capable of realizing automatically entering and exiting an aperture of the gantry 613 in accordance with a preset process to carry the target object to a specified scanning position.

In some embodiments, the surgical robot 620 may include a surgical actuator arm 621, a surgical actuator arm end 623, and a surgical device 625. The surgical actuator arm 621 may be configured to support the surgical actuator arm end 623 and transport the surgical actuator arm end 623 to a designated surgical location. The surgical actuator arm end 623 may be used to secure the surgical device 625 and control the surgical device 625 to perform a surgical action such as puncture, suture, ablation, or the like.

In some embodiments, the control module 630 may be configured to control a target movement state of the surgical robot 620 and/or the imaging device 610 based on an initial movement state of the imaging device 610 and/or the surgical robot 620.

In some embodiments, the control module 630 may be configured to control the surgical robot 620 to remain stationary in response to a determination that the imaging device 610 is in movement, based on a first movement state of the imaging device 610. For example, when the imaging device 610 begins to get into a movement state, a feedback signal may be output to the control module 630, and the control module 630, upon receiving the feedback signal, may output a control signal to the surgical robot 620 to control the moving parts of the surgical robot 620 to get into a locked state.

In some embodiments, the control module 630 may be configured to control the imaging device 610 to remain stationary in response to a determination that the surgical robot 620 is in movement, based on a second movement state of the surgical robot 620. For example, when the surgical robot 620 begins to get into a movement state, a feedback signal may be output to the control module 630, and the control module 630, upon receiving the feedback signal, may output a control signal to the imaging device 610 to control a scanning bed of the imaging device 610 to get into a locked state.

In some embodiments, the control module 630 may control both the imaging device 610 and the surgical robot 620 to remain stationary. For example, the control module 630 may receive a feedback signal output from other modules (e.g., the terminal device 140) and then simultaneously output the control signal to the imaging device 610 as well as the surgical robot 620 to simultaneously control the moving parts of the imaging device 610 and the surgical robot 620 to remain stationary. For example, when the control module 630 detects a failure of the imaging device 610 and/or the surgical robot 620, or an abnormal connection relationship between the two, the control module 630 may simultaneously output a control signal to the imaging device 610 and the surgical robot 620 to simultaneously control the moving parts of the imaging device 610 and the surgical robot 620 to get into the locked state.

In some embodiments, the imaging device 610, as well as the surgical robot 620, may include a holding brake locking structure (not shown in the figures) for locking the moving parts of the imaging device 610 and the surgical robot 620, while the moving parts are held stationary to avoid accidental unnatural movement.

By making one end of the surgical robot and the imaging device remain stationary when the other end is moving, or by controlling the surgical robot and the imaging device to remain stationary at the same time in an unexpected circumstance, the risk of unintended relative movement caused by the independent control of the moving parts of the imaging device and the surgical robot is avoided, thereby improving the safety of the image-guided interventional interposition system 600 in a variety of scenarios.

In some embodiments, the imaging device 610 may be further used to generate a first end signal at an end of a current preset process and transmit the first end signal to the control module 630. In some embodiments, the surgical robot 620 may be configured to generate a second end signal at the end of the current preset process and transmit the second end signal to the control module 630.

The first end signal is a feedback signal generated by the imaging device 610 at the end of the preset process, and the second control signal is a feedback signal generated by the surgical robot 620 at the end of the preset process. The control module 630 receives the first end signal or the second end signal and controls the imaging device 610 and the surgical robot 620 to proceed to a next preset process.

By generating an end signal at an end of each process and sending the end signal to the control module 630, so that the control module 630 controls the imaging device 610 and the surgical robot 620 to get into the next preset process according to the end signal, ensuring interlocked control of the imaging device 610 and the surgical robot 620 when switching between different preset processes, and improving the safety of the image-guided interventional puncture system.

In some embodiments, the control module 630 may be further used to control the imaging device 610 to remain stationary and/or to release a stationary state of the surgical robot 620, based on the first end signal; and/or control, based on the second end signal, the surgical robot 620 to remain stationary, and/or to release a stationary state of the imaging device 610.

Understandably, the surgical robot is ready to move to a next stage of a workflow when the imaging device completes a current workflow, so the moving parts of the imaging device need to be locked, and if the surgical robot is originally in a locked state, it is necessary to unlock the moving parts of the surgical robot. Correspondingly, when the surgical robot completes the current workflow, the imaging device is ready to move to a next stage of a workflow, and therefore needs to lock the moving parts of the surgical robot, and if the imaging device is in the locked state, it needs to unlock the moving parts of the imaging device. It should be noted that when the last two processes are currently being performed by the same device, for example, to transport the patient into the aperture directly after the scanning is completed, the device may be controlled to remain in an unlocked state in order to control the scanning bed to move, thereby transporting the patient into the aperture.

In some embodiments, the imaging device 610 and/or the surgical robot 620 may also be configured to send an access request and an interrupt request to the control module 630. The control module 630 may be configured to control the imaging device 610 and the surgical robot 620 to get into an integral working mode based on the access request, and to control the imaging device 610 and the surgical robot 620 to get into an independent working mode based on the interrupt request. In some embodiments, the control module 630 may be configured to control the imaging device 610 and the surgical robot 620 to get into the independent working mode in response to a failure of the imaging device 610 and/or the surgical robot 620.

In some embodiments, the image-guided interventional puncture system 600 may comprise a first control module and a second control module, wherein the first control module and the second control module control the imaging device 610 and the surgical robot 620, respectively. For example, the first control module is integrated in the imaging device 610 and the second control module is integrated in the surgical robot 620, and by establishing a connection relationship between the first control module and the second control module, the imaging device and the surgical robot may get into the integral working mode. More descriptions about the independent working mode and the integral working mode can be found in FIG. 4 and its related descriptions, and will not be repeated here.

In some embodiments, the control module 630 may be further configured to determine a first movement trajectory of the imaging device 610 based on the first movement state of the imaging device 610 when the imaging device 610 is in movement, and control the surgical robot 620 to move. In some embodiments, the control module 630 may be further configured to control movement speeds of the surgical robot 620 and/or the imaging device 620 based on environmental information and the initial movement states of the imaging device 610 and/or the surgical robot 620. More information can be found in FIG. 3 and its related descriptions, which will not be repeated here.

In some embodiments, the image-guided interventional puncture system 600 may further include a display module 640. The display module 640 may be a module for displaying information such as an image, including, but not limited to, a CRT display, an LCD display, or an LED display.

In some embodiments, the display module 640 may be configured to receive control command information and the movement state information outputted by the imaging device 610 and/or the surgical robot 620, and display the control command information and the movement state information in a display interface. The control command information refers to command information such as the first end signal, the second end signal, or the like. The movement state information refers to the first movement state, the second movement state, and other information reflecting a movement situation (e.g., stationary, movement) of the imaging device 610 and/or the surgical robot 620.

In some embodiments, the display module 640 may display image data (e.g., a scanned image) obtained by the imaging device 610.

In some embodiments, the display module 640 may be coupled with the control module 630, so as to receive a control command as well as operation state information outputted from the imaging device 610 as well as the surgical robot 620 via the control module 630. In some embodiments, when the display module 640 receives the control command information and the movement state information output by the imaging device 610 and/or the surgical robot 620, the information may be displayed on the display interface in a variety of forms. For example, being displayed through text, using a screen to display an image, or using any of a number of ways, such as an image combined with text.

In some embodiments of the present disclosure, by means of the display module, a user (e.g., a physician) may observe the progress of a puncture surgery in real-time based on the control command information output by the imaging device and/or the surgical robot and the movement state information displayed in real-time on the display module, so as to ensure the safety of a surgical process.

Figure 7:
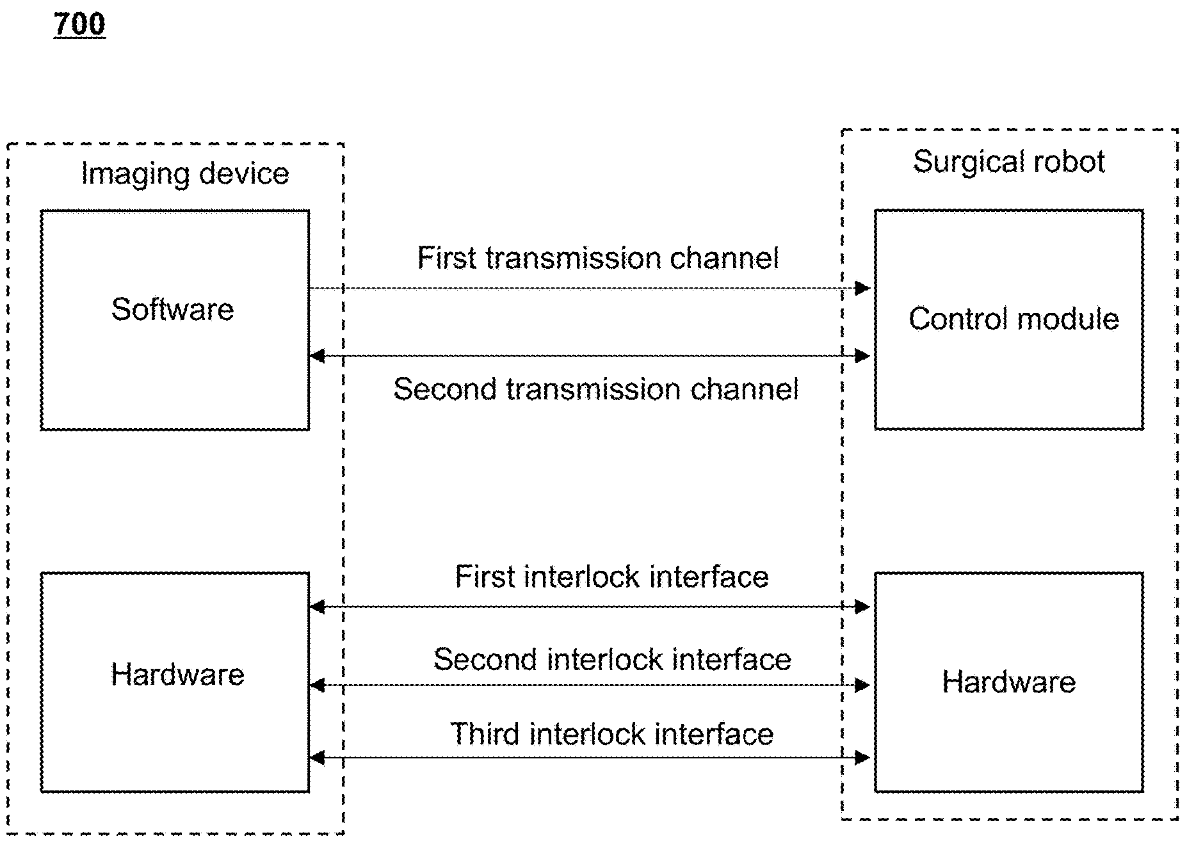
FIG. 7 is a schematic diagram illustrating a connection relationship of the image-guided interventional puncture system according to some embodiments of the present disclosure.

FIG. 7 is a schematic diagram illustrating an exemplary connection relationship of an image-guided interventional puncture system according to some embodiments of the present disclosure.

As shown in FIG. 7, in some embodiments, the connection between an imaging device (e.g., the imaging device 610) and a surgical robot (e.g., the surgical robot 620) in an image-guided interventional puncture system 700 may be divided into levels of hardware and software, with interlocking control realized at a hardware level and interaction of data and/or information (e.g., image data and state information) realized at a software level.

In some embodiments, a hardware connection between the imaging device and the surgical robot may include three interfaces: a first interlock interface, a second interlock interface, and a third interlock interface.

The first interlock interface, which may also be referred to as a safety interlock interface, may be used to control the surgical robot to establish or interrupt the connection relationship with the imaging device, and to detect the connection relationship between the surgical robot and the imaging device. For example, a controller of the surgical robot 620 may be coupled to an interface mounted on a frame (e.g., the gantry 613) of the imaging device 610 via protocol communication.

In some embodiments, after the imaging device is connected to the surgical robot, the imaging device may be identified and calibrated, and gets into an integral working mode after successful calibration, as a means to ensure the connection security of the image-guided interventional puncture system.

The second interlock interface, which may also be referred to as a movement lock interface, may be used to control a movement state of the imaging device based on a movement state of the surgical robot, and/or to control the movement state of the surgical robot based on the movement state of the imaging device. For example, the controller of the surgical robot 620 may be connected via a cable to an interface mounted on a frame (e.g., the gantry 613) of the imaging device 610, and when the surgical robot is in movement, moving parts of the imaging device (e.g., a scanning bed, a gantry) are locked via the second interlock interface, so as to make the imaging device in a stationary state while the surgical robot is in operation, thereby avoiding unintended movement. The moving parts of the imaging device in this mode may be locked by a brake such as a holding brake.

The third interlock interface, which may also be referred to as an emergency stop interface, may be configured to control the moving parts of the imaging device and the surgical robot to remain stationary or get into a locked state in the event of a preset emergency (e.g., a collision, the presence of an obstacle around the device, a physical abnormality in the patient, a surgical abnormality, a device failure, an abnormal connection relationship, etc.). For example, the controller of the surgical robot 620 may be connected via a cable to an interface mounted on a frame (e.g., the gantry 613) of the imaging device 610, triggering an emergency stop of the imaging device 610 when the surgical robot 620 is stopped urgently, triggering an emergency stop of the surgical robot 620 when the imaging device 610 is stopped urgently, or triggering an emergency stop of both the imaging device 610 and the surgical robot 620 when the patient has a physical abnormality, etc. In some embodiments, the third interlock interface may be configured to control the imaging device and/or the surgical robot to move a corresponding distance along a direction opposite to an original movement direction away from a collision object in a preset emergency situation. Thus, unintended movement between the imaging device 610 and the surgical robot 620 is avoided in an emergency situation, ensuring the safety of the image-guided interventional puncture system.

In some embodiments, the first interlock interface, the second interlock interface, and the third interlock interface may be integrated on an interface board of the imaging device or the surgical robot. For example, the imaging device 610 may be connected to the controller of the surgical robot 620 via a bus comprising two cables (for movement lock and emergency stop, respectively) and a communication protocol line.

In some embodiments, the software connection between the imaging device and the surgical robot may include two transmission channels: a first transmission channel and a second transmission channel.

The first transmission channel may be configured to transmit image data. For example, the imaging device 610 may transmit obtained image data to the surgical robot 620 via the first transmission channel to guide the surgical robot 620 to perform a puncture operation based on the image data.

The second transmission channel may be configured to transmit movement state information. For example, the second transmission channel may be configured to transmit first movement state information of the imaging device 110 to the surgical robot 120, and/or second movement state information of the surgical robot 120 to the imaging device 110.

The hardwire transmission channel between the imaging device and the surgical robot is established through a secure interlock interface, which ensures the stability of the interlock structure. Connecting the imaging device and the surgical robot through software enables information interaction between the two devices, enabling the imaging device and the surgical robot to obtain each other's information on time and make adjustments to the surgical surgery, thereby effectively improving the accuracy and execution efficiency of the image-guided interventional puncture system.

The basic concepts have been described above, and it is apparent to those skilled in the art that the foregoing detailed disclosure serves only as an example and does not constitute a limitation of the present disclosure. While not expressly stated herein, a person skilled in the art may make various modifications, improvements, and amendments to the present disclosure. Those types of modifications, improvements, and amendments are suggested in the present disclosure, so those types of modifications, improvements, and amendments remain within the spirit and scope of the exemplary embodiments of the present disclosure.

Also, the present disclosure uses specific words to describe embodiments of the present disclosure. Such as "an embodiment", "one embodiment", and/or "some embodiment" means a feature, structure, or characteristic associated with at least one embodiment of the present disclosure. Accordingly, it should be emphasized and noted that two or more references in the present disclosure to "one embodiment" or "an embodiment" or "an alternative embodiment" in different places in the present disclosure do not necessarily refer to the same embodiment. In addition, certain features, structures, or characteristics in one or more embodiments of the present disclosure may be suitably combined.

Furthermore, unless expressly stated in the claims, the order of the processing elements and sequences, the use of numerical letters, or the use of other names as described in the present disclosure are not intended to qualify the order of the processes and methods of the present disclosure. While some embodiments of the invention that are currently considered useful are discussed in the foregoing disclosure by way of various examples, it is to be understood that such detail serves an illustrative purpose only, and that additional claims are not limited to the disclosed embodiments, rather, the claims are intended to cover all amendments and equivalent combinations that are consistent with the substance and scope of the embodiments of the present disclosure. For example, although the implementation of various components described above may be embodied in a hardware device, it may also be implemented as a software only solution, e.g., an installation on an existing server or mobile device.

Similarly, it should be noted that in order to simplify the presentation of the present disclosure, and thereby aid in the understanding of one or more embodiments of the invention, the foregoing descriptions of embodiments of the present disclosure sometimes combine a variety of features into a single embodiment, accompanying drawings, or descriptions thereof. However, this method of disclosure does not imply that the objects of the present disclosure require more features than those mentioned in the claims. Rather, claimed subject matter may lie in less than all features of a single foregoing disclosed embodiment.

Some embodiments use numbers to describe the number of components, attributes, and it should be understood that such numbers used in the description of the embodiments are modified in some examples by the modifiers "about", "approximately", or "substantially". Unless otherwise noted, the terms "about," "approximately," or "substantially" indicates that a ±20% variation in the stated number is allowed. Correspondingly, in some embodiments, the numerical parameters used in the present disclosure and claims are approximations, which can change depending on the desired characteristics of individual embodiments. In some embodiments, the numerical parameters should take into account the specified number of valid digits and utilize a general digit retention method. While the numerical domains and parameters used to confirm the breadth of their ranges in some embodiments of the present disclosure are approximations, in specific embodiments, such values are set to be as precise as possible within a feasible range.

For each of the patents, patent applications, patent application disclosures, and other materials cited in the present disclosure, such as articles, books, specification sheets, publications, documents, or the like, are hereby incorporated by reference in their entirety into the present disclosure. Application history documents that are inconsistent with or conflict with the contents of the present disclosure are excluded, as are documents (currently or hereafter appended to the present disclosure) that limit the broadest scope of the claims of the present disclosure. It should be noted that in the event of any inconsistency or conflict between the descriptions, definitions, and/or use of terms in the materials appended to the present disclosure and those set forth herein, the descriptions, definitions and/or use of terms in the present disclosure shall prevail.

Finally, it should be understood that the embodiments described in the present disclosure are only used to illustrate the principles of the embodiments of the present disclosure. Other deformations may also fall within the scope of the present disclosure. As such, alternative configurations of embodiments of the present disclosure may be viewed as consistent with the teachings of the present disclosure as an example, not as a limitation. Correspondingly, the embodiments of the present disclosure are not limited to the embodiments expressly presented and described herein.

What is claimed is:

1. A method for controlling an image-guided interventional puncture device, comprising:

obtaining an initial movement state of an imaging device and surgical robot, the surgical robot being a robotic arm body for driving a robotic arm end in movement to control and/or adjust an operation and/or attitude of a functional component carried by the robotic arm end;

controlling a target movement state of the surgical robot and/or the imaging device based on the initial movement state, including:

controlling a second movement state of the surgical robot based on a first movement state of the imaging device, including:

in response to a determination that the imaging device is in movement, locking a moving part of the surgical robot to control the surgical robot to remain stationary based on the first movement state of the imaging device; and/or controlling the first movement state of the imaging device based on the second movement state of the surgical robot, including:

in response to a determination that the surgical robot is in movement, locking a moving part of the imaging device to control the imaging device to remain stationary based on the second movement state of the surgical robot;

controlling, based on an access request from the surgical robot or the imaging device, the imaging device and the surgical robot to get into an integral working mode, wherein movement states of the imaging device and the surgical robot are mutually associated in the integral working mode;

in the integral working mode, detecting a working state of hardware interface and software interface of the imaging device and the surgical robot;

controlling the imaging device and the surgical robot to enter into a locked state when an abnormal condition exists in an interface cable or software;

performing self-repair by the surgical robot or the imaging device after entering the locked state;

resuming operation of the imaging device and the surgical robot after receiving a user confirmation signal when the self-repair fails; and in response to a failure of the imaging device or the surgical robot, controlling the imaging device and the surgical robot to get into an independent working mode;

capturing an image of a target object in real-time by a camera, and when the presence of unintended movement of the target object is recognized based on the captured image, controlling the imaging device and the surgical robot to remain stationary at the same time.

2. The method of claim 1, wherein the controlling a second movement state of the surgical robot based on a first movement state of the imaging device includes:

determining a first movement trajectory of the imaging device based on the first movement state of the imaging device; and controlling, based on the first movement trajectory, the surgical robot to move.

3. The method of claim 2, wherein the controlling, based on the first movement trajectory, the surgical robot to move includes:

predicting a distance between the imaging device and the surgical robot based on the first movement trajectory of the imaging device; and in response to the distance being less than a distance threshold, controlling both the imaging device and the surgical robot to remain stationary.

4. The method of claim 1, further comprising:

controlling a movement speed of the surgical robot and the imaging device based on environmental information.

5. The method of claim 4, further comprising:

controlling the surgical robot to reduce the speed when the surgical robot is moving toward the target object, and at this time the target object raises a hand;

controlling the surgical robot to return to an original speed when the hand of the target object is put back to an original position; and controlling the imaging device to stop moving when the surgical robot stops moving and the distance between the imaging device and the surgical robot decreases.

6. The method of claim 1, further comprising:

obtaining a first end signal generated by the imaging device at an end of a current preset process, or a second end signal generated by the surgical robot at the end of the current preset process; and controlling a movement state of the imaging device and/or the surgical robot in a next process based on the first end signal or the second end signal.

7. The method of claim 6, wherein the controlling the movement state of the imaging device and/or the surgical robot in a next process based on the first end signal or the second end signal includes:

controlling the imaging device to remain stationary, and/or be released from a stationary state of the surgical robot, based on the first end signal; and controlling the surgical robot to remain stationary, and/or be released from a stationary state of the imaging device, based on the second end signal.

8. The method of claim 7, further comprising:

in response to the current preset process and the next process being executed by a same device, maintaining the imaging device or the surgical robot in an unlocked state after receiving the first end signal or the second end signal, so as to continuously execute the next process.

9. The method of claim 8, wherein the current preset process and the next process correspond to work tasks of individual stages in a complete preset process, the complete preset process being determined based on patient information, and the work tasks of the individual stages being executed separately by the imaging device or the surgical robot.

10. The method of claim 1, further comprising:

obtaining an interrupt request sent by the imaging device or the surgical robot; and controlling, based on the interrupt request, the imaging device and the surgical robot to get into an independent working mode, wherein the movement states of the imaging device and the surgical robot are independent of each other in the independent working mode.

11. The method of claim 1, further comprising:

detecting a connection relationship between the imaging device and the surgical robot; and in response to the connection relationship being abnormal, controlling both the imaging device and the surgical robot to remain stationary.

12. A system for controlling an image-guided interventional puncture device, comprising:

an imaging device, configured to obtain image data of a target object;

a surgical robot, configured to perform a puncture operation; and a control module, configured to control a target movement state of the surgical robot and the imaging device based on an initial movement state of the imaging device and the surgical robot, wherein the surgical robot being a robotic arm body for driving a robotic arm end in movement to control and/or adjust an operation and/or attitude of a functional component carried by the robotic arm end;

to control the target movement state of the surgical robot and/or the imaging device based on the initial movement state of the imaging device and/or the surgical robot, the control module is configured to:

control a second movement state of the surgical robot based on a first movement state of the imaging device, including:

in response to a determination that the imaging device is in movement, locking a moving part of the surgical robot to control the surgical robot to remain stationary based on the first movement state of the imaging device; and/or control the first movement state of the imaging device based on the second movement state of the surgical robot, including:

in response to a determination that the surgical robot is in movement, locking a moving part of the imaging device to control the imaging device to remain stationary based on the second movement state of the surgical robot;

controlling, based on an access request from the surgical robot or the imaging device, the imaging device and the surgical robot to get into an integral working mode, wherein movement states of the imaging device and the surgical robot are mutually associated in the integral working mode;

in the integral working mode, detecting a working state of hardware interface and software interface of the imaging device and the surgical robot;

controlling the imaging device and the surgical robot to enter into a locked state when an abnormal condition exists in an interface cable or software;

performing self-repair by the surgical robot or the imaging device after entering the locked state; and resuming operation of the imaging device and the surgical robot after receiving a user confirmation signal when the self-repair fails;

in response to a failure of the imaging device or the surgical robot, controlling the imaging device and the surgical robot to get into an independent working mode;

capturing an image of a target object in real-time by a camera, and when the presence of unintended movement of the target object is recognized based on the captured image, controlling the imaging device and the surgical robot to remain stationary at the same time.

13. The system of claim 12, further comprising:

a display module, configured to receive control command information and movement status information output by the imaging device and/or the surgical robot and display the information in a display interface.

14. The system of claim 12, further comprising:

a first interlock interface, configured to control the surgical robot to establish or interrupt a connection relationship with the imaging device, and to detect the connection relationship;

a second interlock interface, configured to control a movement state of the imaging device based on a movement state of the surgical robot; and a third interlock interface, configured to control the imaging device and/or the surgical robot to remain stationary in a preset emergency situation.

15. The system of claim 12, further comprising:

a first transmission channel, configured to transmit the image data obtained by the imaging device to the surgical robot to cause the surgical robot to perform the puncture operation based on the image data; and a second transmission channel, configured to transmit first movement state information of the imaging device to the surgical robot, and/or transmit second movement state information of the surgical robot to the imaging device.

16. A non-transitory computer readable storage medium, comprising at least one set of instructions, wherein when executed by at least one processor of a computer device, the at least one set of instructions directs the at least one processor to perform a method including:

obtaining an initial movement state of an imaging device and a surgical robot, the surgical robot being a robotic arm body for driving a robotic arm end in movement to control and/or adjust an operation and/or attitude of a functional component carried by the robotic arm end;

controlling a target movement state of the surgical robot and/or the imaging device based on the initial movement state, including:

controlling a second movement state of the surgical robot based on a first movement state of the imaging device, including:

in response to a determination that the imaging device is in movement, locking a moving part of the surgical robot to control the surgical robot to remain stationary based on the first movement state of the imaging device; and/or controlling the first movement state of the imaging device based on the second movement state of the surgical robot, including:

in response to a determination that the surgical robot is in movement, locking a moving part of the imaging device to control the imaging device to remain stationary based on the second movement state of the surgical robot;

controlling, based on an access request from the surgical robot or the imaging device, the imaging device and the surgical robot to get into an integral working mode, wherein movement states of the imaging device and the surgical robot are mutually associated in the integral working mode;

in the integral working mode, detecting a working state of hardware interface and software interface of the imaging device and the surgical robot;

controlling the imaging device and the surgical robot to enter into a locked state when an abnormal condition exists in an interface cable or software;

performing self-repair by the surgical robot or the imaging device after entering the locked state; and resuming operation of the imaging device and the surgical robot after receiving a user confirmation signal when the self-repair fails; and in response to a failure of the imaging device or the surgical robot, controlling the imaging device and the surgical robot to get into an independent working mode;

capturing an image of a target object in real-time by a camera, and when the presence of unintended movement of the target object is recognized based on the captured image, controlling the imaging device and the surgical robot to remain stationary at the same time.

* * * * *